(12) United States Patent
Boronkay et al.

(10) Patent No.: US 9,375,298 B2
(45) Date of Patent: Jun. 28, 2016

(54) DENTAL MODELS AND RELATED METHODS

(71) Applicant: Align Technology, Inc., San Jose, CA (US)

(72) Inventors: Allen R. Boronkay, San Jose, CA (US); Avi Kopelman, Palo Alto, CA (US); Srinivas Kaza, San Francisco, CA (US)

(73) Assignee: ALIGN TECHNOLOGY, INC., San Jose, CA (US)

( * ) Notice: Subject to any disclaimer, the term of this patent is extended or adjusted under 35 U.S.C. 154(b) by 263 days.

(21) Appl. No.: 13/773,229

(22) Filed: Feb. 21, 2013

(65) Prior Publication Data

US 2013/0216980 A1    Aug. 22, 2013

Related U.S. Application Data

(60) Provisional application No. 61/601,448, filed on Feb. 21, 2012.

(51) Int. Cl.
| | |
|---|---|
| *A61C 11/00* | (2006.01) |
| *A61C 13/34* | (2006.01) |
| *A61C 13/00* | (2006.01) |
| *A61C 5/10* | (2006.01) |
| *A61C 8/00* | (2006.01) |
| *A61C 9/00* | (2006.01) |

(52) U.S. Cl.
CPC . *A61C 13/34* (2013.01); *A61C 5/10* (2013.01); *A61C 8/00* (2013.01); *A61C 9/002* (2013.01); *A61C 13/0003* (2013.01)

(58) Field of Classification Search
CPC .... A61C 13/37; A61C 13/34; A61C 13/0003; A61C 5/10; A61C 8/00

USPC .......................................... 433/213, 172–176
See application file for complete search history.

(56) References Cited

U.S. PATENT DOCUMENTS

| | | | |
|---|---|---|---|
| 2,467,432 A | 4/1949 | Kesling | |
| 3,286,350 A * | 11/1966 | Cooper | A61C 9/002 164/108 |
| 3,407,500 A | 10/1968 | Kesling | |
| 3,600,808 A | 8/1971 | Reeve | |
| 3,660,900 A | 5/1972 | Andrews | |
| 3,683,502 A | 8/1972 | Wallshein | |

(Continued)

FOREIGN PATENT DOCUMENTS

| | | |
|---|---|---|
| AU | 3031677 A | 5/1979 |
| AU | 517102 B2 | 7/1981 |

(Continued)

OTHER PUBLICATIONS

AADR. American Association for Dental Research, Summary of Activities, Mar. 20-23,1980, Los ngeles, CA, p. 195.

(Continued)

*Primary Examiner* — Yogesh Patel
(74) *Attorney, Agent, or Firm* — Wilson Sonsini Goodrich & Rosati

(57) ABSTRACT

A dental model and related systems and methods, including a first component representing a portion of a patient's jaw and a second component that is demountably attachable to the first component, and a second component representing a dental structure of interest, such as the remaining portion of a tooth or a dental implant.

20 Claims, 13 Drawing Sheets

(56) References Cited

U.S. PATENT DOCUMENTS

| | | |
|---|---|---|
| 3,738,005 A | 6/1973 | Cohen |
| 3,860,803 A | 1/1975 | Levine |
| 3,916,526 A | 11/1975 | Schudy |
| 3,922,786 A | 12/1975 | Lavin |
| 3,950,851 A | 4/1976 | Bergersen |
| 3,983,628 A | 10/1976 | Acevedo |
| 4,014,096 A | 3/1977 | Dellinger |
| 4,195,046 A | 3/1980 | Kesling |
| 4,253,828 A | 3/1981 | Coles et al. |
| 4,324,546 A | 4/1982 | Heitlinger et al. |
| 4,324,547 A | 4/1982 | Arcan et al. |
| 4,348,178 A | 9/1982 | Kurz |
| 4,478,580 A | 10/1984 | Barrut |
| 4,500,294 A | 2/1985 | Lewis |
| 4,504,225 A | 3/1985 | Yoshii |
| 4,505,673 A | 3/1985 | Yoshii |
| 4,526,540 A | 7/1985 | Dellinger |
| 4,575,330 A | 3/1986 | Hull |
| 4,575,805 A | 3/1986 | Moermann et al. |
| 4,591,341 A | 5/1986 | Andrews |
| 4,609,349 A | 9/1986 | Cain |
| 4,611,288 A | 9/1986 | Duret et al. |
| 4,656,860 A | 4/1987 | Orthuber et al. |
| 4,663,720 A | 5/1987 | Duret et al. |
| 4,664,626 A | 5/1987 | Kesling |
| 4,676,747 A | 6/1987 | Kesling |
| 4,742,464 A | 5/1988 | Duret et al. |
| 4,755,139 A | 7/1988 | Abbatte et al. |
| 4,763,791 A | 8/1988 | Halverson et al. |
| 4,793,803 A | 12/1988 | Martz |
| 4,798,534 A | 1/1989 | Breads |
| 4,836,778 A | 6/1989 | Baumrind et al. |
| 4,837,732 A | 6/1989 | Brandestini et al. |
| 4,850,864 A | 7/1989 | Diamond |
| 4,850,865 A | 7/1989 | Napolitano |
| 4,856,991 A | 8/1989 | Breads et al. |
| 4,877,398 A | 10/1989 | Kesling |
| 4,880,380 A | 11/1989 | Martz |
| 4,889,238 A | 12/1989 | Batchelor |
| 4,890,608 A | 1/1990 | Steer |
| 4,935,635 A | 6/1990 | O'Harra |
| 4,936,862 A | 6/1990 | Walker et al. |
| 4,937,928 A | 7/1990 | van der Zel |
| 4,941,826 A | 7/1990 | Loran et al. |
| 4,964,770 A | 10/1990 | Steinbichler et al. |
| 4,975,052 A | 12/1990 | Spencer et al. |
| 4,983,334 A | 1/1991 | Adell |
| 5,011,405 A | 4/1991 | Lemchen |
| 5,017,133 A | 5/1991 | Miura |
| 5,027,281 A | 6/1991 | Rekow et al. |
| 5,035,613 A | 7/1991 | Breads et al. |
| 5,055,039 A | 10/1991 | Abbatte et al. |
| 5,059,118 A | 10/1991 | Breads et al. |
| 5,100,316 A | 3/1992 | Wildman |
| 5,106,299 A * | 4/1992 | Ghalili ............... A61C 8/0048 433/172 |
| 5,121,333 A | 6/1992 | Riley et al. |
| 5,125,832 A | 6/1992 | Kesling |
| 5,128,870 A | 7/1992 | Erdman et al. |
| 5,130,064 A | 7/1992 | Smalley |
| 5,131,843 A | 7/1992 | Hilgers et al. |
| 5,131,844 A | 7/1992 | Marinaccio et al. |
| 5,139,419 A | 8/1992 | Andreiko et al. |
| 5,145,364 A | 9/1992 | Martz et al. |
| 5,176,517 A | 1/1993 | Truax |
| 5,184,306 A | 2/1993 | Erdman et al. |
| 5,186,623 A | 2/1993 | Breads et al. |
| 5,197,874 A * | 3/1993 | Silva ..................... A61C 9/002 433/34 |
| 5,257,203 A | 10/1993 | Riley et al. |
| 5,273,429 A | 12/1993 | Rekow et al. |
| 5,278,756 A | 1/1994 | Lemchen et al. |
| 5,328,362 A | 7/1994 | Watson et al. |
| 5,338,198 A | 8/1994 | Wu et al. |
| 5,340,309 A | 8/1994 | Robertson |
| 5,342,202 A | 8/1994 | Deshayes |
| 5,368,478 A | 11/1994 | Andreiko et al. |
| 5,382,164 A | 1/1995 | Stern |
| 5,395,238 A | 3/1995 | Andreiko et al. |
| 5,431,562 A | 7/1995 | Andreiko et al. |
| 5,440,326 A | 8/1995 | Quinn |
| 5,440,496 A | 8/1995 | Andersson et al. |
| 5,447,432 A | 9/1995 | Andreiko et al. |
| 5,452,219 A | 9/1995 | Dehoff et al. |
| 5,454,717 A | 10/1995 | Andreiko et al. |
| 5,456,600 A | 10/1995 | Andreiko et al. |
| 5,474,448 A | 12/1995 | Andreiko et al. |
| RE35,169 E | 3/1996 | Lemchen et al. |
| 5,518,397 A | 5/1996 | Andreiko et al. |
| 5,528,735 A | 6/1996 | Strasnick et al. |
| 5,533,895 A | 7/1996 | Andreiko et al. |
| 5,542,842 A | 8/1996 | Andreiko et al. |
| 5,549,476 A | 8/1996 | Stern |
| 5,562,448 A | 10/1996 | Mushabac |
| 5,587,912 A | 12/1996 | Andersson et al. |
| 5,605,459 A | 2/1997 | Kuroda et al. |
| 5,607,305 A | 3/1997 | Andersson et al. |
| 5,614,075 A | 3/1997 | Andre |
| 5,621,648 A | 4/1997 | Crump |
| 5,645,420 A | 7/1997 | Bergersen |
| 5,645,421 A | 7/1997 | Slootsky |
| 5,655,653 A | 8/1997 | Chester |
| 5,683,243 A | 11/1997 | Andreiko et al. |
| 5,692,894 A | 12/1997 | Schwartz et al. |
| 5,725,376 A | 3/1998 | Poirier |
| 5,725,378 A | 3/1998 | Wang |
| 5,733,126 A | 3/1998 | Andersson et al. |
| 5,740,267 A | 4/1998 | Echerer et al. |
| 5,742,700 A | 4/1998 | Yoon et al. |
| 5,788,490 A * | 8/1998 | Huffman ........................ 433/74 |
| 5,799,100 A | 8/1998 | Clarke et al. |
| 5,800,174 A | 9/1998 | Andersson |
| 5,823,778 A | 10/1998 | Schmitt et al. |
| 5,848,115 A | 12/1998 | Little et al. |
| 5,857,853 A | 1/1999 | van Nifterick et al. |
| 5,866,058 A | 2/1999 | Batchelder et al. |
| 5,879,158 A | 3/1999 | Doyle et al. |
| 5,880,961 A | 3/1999 | Crump |
| 5,880,962 A | 3/1999 | Andersson et al. |
| 5,934,288 A | 8/1999 | Avila et al. |
| 5,957,686 A | 9/1999 | Anthony |
| 5,964,587 A | 10/1999 | Sato |
| 5,971,754 A | 10/1999 | Sondhi et al. |
| 5,975,893 A | 11/1999 | Chishti et al. |
| 6,015,289 A | 1/2000 | Andreiko et al. |
| 6,044,309 A | 3/2000 | Honda |
| 6,049,743 A | 4/2000 | Baba |
| 6,062,861 A | 5/2000 | Andersson |
| 6,068,482 A | 5/2000 | Snow |
| 6,099,314 A | 8/2000 | Kopelman et al. |
| 6,116,070 A * | 9/2000 | Oshida et al. ..................... 72/60 |
| 6,123,544 A | 9/2000 | Cleary |
| 6,152,731 A | 11/2000 | Jordan et al. |
| 6,183,248 B1 | 2/2001 | Chishti et al. |
| 6,190,165 B1 | 2/2001 | Andreiko et al. |
| 6,217,325 B1 | 4/2001 | Chishti et al. |
| 6,217,334 B1 | 4/2001 | Hultgren |
| 6,244,861 B1 | 6/2001 | Andreiko et al. |
| 6,309,215 B1 | 10/2001 | Phan et al. |
| 6,315,553 B1 | 11/2001 | Sachdeva et al. |
| 6,322,359 B1 | 11/2001 | Jordan et al. |
| 6,350,120 B1 | 2/2002 | Sachdeva et al. |
| 6,382,975 B1 | 5/2002 | Poirier |
| 6,398,548 B1 | 6/2002 | Muhammad et al. |
| 6,402,707 B1 | 6/2002 | Ernst |
| 6,482,298 B1 | 11/2002 | Bhatnagar |
| 6,524,101 B1 | 2/2003 | Phan et al. |
| 6,554,611 B2 | 4/2003 | Chishti et al. |
| 6,572,372 B1 | 6/2003 | Phan et al. |
| 6,629,840 B2 | 10/2003 | Chishti et al. |
| 6,705,863 B2 | 3/2004 | Phan et al. |
| 6,719,562 B1 * | 4/2004 | Oestreich ............. G09B 23/283 433/213 |
| 6,722,880 B2 | 4/2004 | Chishti et al. |

(56) References Cited

U.S. PATENT DOCUMENTS

| | | | |
|---|---|---|---|
| 2002/0006597 A1 | 1/2002 | Andreiko et al. | |
| 2003/0009252 A1 | 1/2003 | Pavlovskaia et al. | |
| 2003/0139834 A1 | 7/2003 | Nikolskiy et al. | |
| 2003/0203334 A1* | 10/2003 | Hedge et al. | 433/53 |
| 2003/0211444 A1* | 11/2003 | Andrews | 433/172 |
| 2003/0224311 A1 | 12/2003 | Cronauer | |
| 2004/0128010 A1 | 7/2004 | Pavlovskaia et al. | |
| 2005/0055118 A1 | 3/2005 | Nikolskiy et al. | |
| 2007/0212663 A1* | 9/2007 | Oestreich | A61C 11/00 433/213 |
| 2011/0236849 A1* | 9/2011 | Pogorelsky | A61C 7/00 433/24 |
| 2012/0237903 A1* | 9/2012 | Klare et al. | 433/213 |

FOREIGN PATENT DOCUMENTS

| | | |
|---|---|---|
| AU | 5598894 A | 6/1994 |
| CA | 1121955 | 4/1982 |
| DE | 2749802 | 5/1978 |
| DE | 69327661 T | 7/2000 |
| EP | 0091876 A1 | 10/1983 |
| EP | 0299490 A2 | 1/1989 |
| EP | 0376873 A2 | 7/1990 |
| EP | 0490848 A2 | 6/1992 |
| EP | 0541500 A1 | 5/1993 |
| EP | 0667753 B1 | 8/1995 |
| EP | 0731673 B1 | 9/1996 |
| EP | 0774933 B1 | 5/1997 |
| ES | 463897 | 1/1980 |
| FR | 2369828 A1 | 6/1978 |
| FR | 2652256 A1 | 3/1991 |
| GB | 15500777 | 8/1979 |
| JP | 53-058191 | 5/1978 |
| JP | 04-028359 | 1/1992 |
| JP | 08-508174 | 9/1996 |
| WO | WO 90/08512 A1 | 8/1990 |
| WO | WO 91/04713 A1 | 4/1991 |
| WO | WO 94/10935 A1 | 5/1994 |
| WO | WO 98/32394 A1 | 7/1998 |
| WO | WO 98/44865 A1 | 10/1998 |
| WO | WO 98/58596 A1 | 12/1998 |

OTHER PUBLICATIONS

Alcaniz, et aL, "An Advanced System for the Simulation and Planning of Orthodontic Treatments," Karl HF Heinz Hohne and Ron Kikinis (eds.), Visualization in Biomedical Computing, 4th Intl. Conf., VBC '96, Hamburg, Germany, Sep. 22-25, 1996, Springer-Verlag, pp. 511-520.

Alexander et al., "The DigiGraph Work Station Part 2 Clinical Management," JCO, pp. 402-407 (Jul. 1990.

Altschuler et al., "Analysis of 3-D Data for Comparative 3-D Serial Growth Pattern Studies of Oral-Facial Structures," AADR Abstracts, Program and Abstracts of Papers, 57th General Session, IADR HP Annual Session, Mar. 29, 1979-Apr. 1, 1979, New Orleans Marriot, Journal of Dental Research, vol. 58, Jan. 1979, Special Issue A, p. 221.

Altschuler et al., "Laser Electro-Optic System for Rapid Three-Dimensional (3D) Topographic Mapping of Surfaces," Optical Engineering, 20(6):953-961 (1981).

Altschuler et al., "Measuring Surfaces Space-Coded by a Laser-Projected Dot Matrix," SPIE Imaging q Applications for Automated Industrial Inspection and Assembly, vol. 182, p. 187-191 (1979).

Altschuler, "3D Mapping of Maxillo-Facial Prosthesis," AADR Abstract #607, 2 pages total, (1980).

Andersson et al., "Clinical Results with Titanium Crowns Fabricated with Machine Duplication and Spark Erosion," Acta. Odontol. Scand., 47:279-286 (1989).

Andrews, The Six Keys to Optimal Occlusion Straight Wire, Chapter 3, pp. 13-24 (1989).

Bartels, et al., An Introduction to Splines for Use in Computer Graphics and Geometric Modeling, Morgan Kaufmann Publishers, pp. 422-425 (1987).

Baumrind et al., "A Stereophotogrammetric System for the Detection of Prosthesis Loosening in Total Hip Arthroplasty," NATO Symposium on Applications of Human Biostereometrics, Jul. 9-13, 1978, SPIE, vol. 166, pp. 112-123.

Baumrind et al., "Mapping the Skull in 3-D," reprinted from J. Calif. Dent. Assoc., 48(2), 11 pages total, (1972 Fall Issue).

Baumrind, "A System for Craniofacial Mapping Through the Integration of Data from Stereo X-Ray Films and Stereo Photographs," an invited paper submitted to the 1975 American Society of Photogram Symposium on Close-Range Photogram Systems, University of III., Aug. 26-30, 1975, pp. 142-166.

Baumrind, "Integrated Three-Dimensional Craniofacial Mapping: Background, Principles, and Perspectives," Semin in Orthod., 7(4):223-232 (Dec. 2001).

Begole et al., "A Computer System for the Analysis of Dental Casts," The Angle Orthod., 51(3):253-259 (Jul. 1981).

Bernard et al.,"Computerized Diagnosis in Orthodontics for Epidemiological Studies: A Progress Report," Abstract, J. Dental Res. Special Issue, vol. 67, p. 169, paper presented at International Association for Dental Research 66th General Session, Mar. 9-13, 1988, Montreal, Canada.

Bhatia et al., "A Computer-Aided Design for Orthognathic Surgery," Br. J. Oral Maxillofac. Surg., 22:237-253 (1984).

Biggerstaff et al., "Computerized Analysis of Occlusion in the Postcanine Dentition," Am. J. Orthod., 61(3): 245-254 (Mar. 1972).

Biggerstaff, "Computerized Diagnostic Setups and Simulations," Angle Orthod., 40(1):28-36 (Jan. 1970).

Biostar Opeation & Training Manual. Great Lakes Orthodontics, Ltd. 199 Fire Tower Drive, Tonawanda, New York. 14150-5890, 20 pages total (1990).

Blu, et al., "Linear interpolation revitalized", IEEE Trans. Image Proc., 13(5):710-719 (May 2004).

Bourke, "Coordinate System Transformation," (Jun. 1996), p. 1, retrieved from the Internet Nov. 5, 2004,URL <http://astronomy.swin.edu.au/-pbourke/prolection/coords>.

Boyd et al., "Three Dimensional Diagnosis and Orthodontic Treatment of Complex Malocclusions With the Invisalipn Appliance," Semin. Orthod., 7(4):274-293 (Dec. 2001).

Brandestini et al., "Computer Machined Ceramic Inlays: In Vitro Marginal Adaptation," J. Dent. Res. Special Issue, Abstract 305, vol. 64, p. 208 (1985).

Brook et al., "An Image Analysis System for the Determination of Tooth Dimensions from Study Casts: IK Comparison with Manual Measurements of Mesio-distal Diameter," J. Dent. Res., 65(3):428-431 (Mar. 1986).

Burstone (interview), "Dr. Charles J. Burstone on the Uses of the Computer in Orthodontic Practice (Part 1)," J. Clin. Orthod., 13(7):442-453 (Jul. 1979).

Burstone (interview), "Dr. Charles J. Burstone on the Uses of the Computer in Orthodontic Practice (Part 2)," J. Clin. Orthod., 13(8):539-551 (Aug. 1979.

Burstone et al., Precision Adjustment of the Transpalatal Lingual Arch: Computer Arch Form in Predetermination, Am, Journal of Orthodontics, vol. 79, No. 2 (Feb. 1981), pp. 115-133.

Cardinal Industrial Finishes, Powder Coatings information posted at <http://www.cardinalpaint.com> on Aug. 25, 2000, 2 pages.

Carnaghan, "An Alternative to Holograms for the Portrayal of Human Teeth," 4th Intl. Conf. on Holographic Systems, Components and Applications, Sep. 15, 1993, pp. 228-231.

Chaconas et al., "The DigiGraph Work Station, Part 1, Basic Concepts," JCO, pp. 360-367 (Jun. 1990).

Chafetz et al., "Subsidence of the Femoral Prosthesis, A Stereophotogrammetric Evaluation," Clin. Orthop. Relat. Res., No. 201, pp. 60-67 (Dec. 1985).

Chiappone, (1980). Constructing the Gnathologic Setup and Positioner, J. Clin. Orthod, vol. 14, pp. 121-133.

Cottingham, (1969). Gnathologic Clear Plastic Positioner, Am. J. Orthod, vol. 55, pp. 23-31.

Crawford, "CAD/CAM in the Dental Office: Does It Work?", Canadian Dental Journal, vol. 57, No. 2, pp. 121-123 (Feb. 1991).

(56) References Cited

OTHER PUBLICATIONS

Crawford, "Computers in Dentistry: Part 1: CAD/CAM: The Computer Moves Chairside," "Part 2: F. Duret—A Man With a Vision," "Part 3: The Computer Gives New Vision—Literally, " "Part 4: Bytes 'N Bites" The Comptuer Moves From the Front Desk to the Operatory, Canadian Dental Journal, vol. 54(9), pp. 661-666 (1988).

Crooks, "CAD/CAM Comes to USC," USC Dentistry, pp. 14-17 (Spring 1990).

Cureton, Correcting Malaligned Mandibular Incisors with Removable Retainers, J. Clin. Orthod, vol. 30, No. 7 (1996) pp. 390-395.

Curry et al., "Integrated Three-Dimensional Craniofacial Mapping at the Craniofacial Research Instrumentation Laboratory/University of the Pacific," Semin Orthod., 7(4):258-265 (Dec. 2001).

Cutting et al., "Three-Dimensional Computer-Assisted Design of Craniofacial Surgical Procedures: Optimization and Interaction with Cephalometric and CT-Based Models," Plast. 77(6):877-885 (Jun. 1986).

DCS Dental AG, "The CAD/CAM 'DCS Titan System' for Production of Crowns/Bridges," DSC Production AG, pp. 1-7 (Jan. 1992).

Definition for gingiva. Dictionary.com p. 1-3. Retrieved from the internet Nov. 5, 2004 <http://reference.com/search/search?q=gingiva>.

DeFranco et al., "Three-Dimensional Large Displacement Analysis of Orthodontic Appliances," J. Biomechanics, 9:793-801 (1976).

Dental Institute University of Zurich Switzerland, Program for International Symposium JD on Computer Restorations: State of the Art of the CEREC-Method, May 1991, 2 pages total.

Dentrac Corporation, Dentrac document, pp. 4-13 (1992).

Dent-X posted on Sep. 24, 1998 at <http://www.dent-x.com/DentSim.htm>, 6 pages.

Doyle, "Digital Dentistry," Computer Graphics World, pp. 50-52, 54 (Oct. 2000).

DuraClearTM product information, Allesee Orthodontic Appliances-Pro Lab, 1 page. (1997).

Duret et al, "CAD-CAM in Dentistry," J. Am. Dent. Assoc. 117:715-720 (Nov. 1988.

Duret et al., "CAD/CAM Imaging in Dentistry," Curr. Opin. Dent., 1:150-154 (1991.

Duret, "The Dental CAD/CAM, General Description of the Project," Hennson International Product Brochure, 18 pages total, Jan. 1986.

Duret,"Vers Une Prothese Informatisee," (English translation attached), Tonus, vol. 75, pp. 55-57 (Nov. 15, 1985).

Economides, "The Microcomputer in the Orthodontic Office," JCO, pp. 767-772 (Nov. 1979.

Elsasser, Some Observations on the History and Uses of the Kesling Positioner, Am. J. Orthod. (1950) 36:368-374.

English translation of Japanese Laid-Open Publication No. 63-11148 to inventor T. Ozukuri (Laid-Open on Jan. 18, 1998) pp. 1-7.

Felton et al., "A Computerized Analysis of the Shape and Stability of Mandibular Arch Form," Am. J. Orthod. Dentofacial Orthop., 92(6):478-483 (Dec. 1987.

Friede et al., "Accuracy of Cephalometric Prediction in Orthognathic Surgery," Abstract of Papers, J. Dent. Res., 70:754-760 (1987.

Futterling et al., "Automated Finite Element Modeling of a Human Mandible with Dental Implants," JS WSCG '98 -Conference Program, retrieved from the Internet: <http://wscg.zcu.cz/wscg98/papers98/Strasser 98.pdf>, 8 pages.

Gao et al., "3-D element Generation for Multi-Connected Complex Dental and Mandibular Structure," Proc. Intl Workshop on Medical Imaging and Augmented Reality, pp. 267-271 (Jun. 12, 2001.

Gim-Alldent Deutschland, "Das DUX System: Die Technik," 2 pages total (2002).

Gottleib et al., "JCO Interviews Dr. James A. McNamara, Jr., on the Frankel Appliance: Part 2: Clinical 1-1 Management, "J. Clin. Orthod., 16(6):390-407 (Jun. 1982.

Grayson, "New Methods for Three Dimensional Analysis of Craniofacial Deformity, Symposium: JW Computerized Facial Imaging in Oral and Maxiiofacial Surgery," AAOMS, 3 pages total, (Sep. 13, 1990).

Guess et al., "Computer Treatment Estimates in Orthodontics and Orthognathic Surgery," JCO, pp. 262-228 (Apr. 1989.

Heaven et al., "Computer-Based Image Analysis of Artificial Root Surface Caries," Abstracts of Papers, J. Dent. Res., 70:528 (Apr. 17-21, 1991.

Highbeam Research, "Simulating Stress Put on Jaw," Tooling & Production [online], Nov. 1996, n pp. 1-2, retrieved from the Internet on Nov. 5, 2004, URL http://static.highbeam.com/t/toolingamp-production/november011996/simulatingstressputonfa . . . >.

Hikage, "Integrated Orthodontic Management System for Virtual Three-Dimensional Computer Graphic Simulation and Optical Video Image Database for Diagnosis and Treatment Planning", Journal of Japan KA Orthodontic Society, Feb. 1987, English translation, pp. 1-38, Japanese version, 46(2), pp. 248-269 (60 pages total.

Hoffmann, et al., "Role of Cephalometry for Planning of Jaw Orthopedics and Jaw Surgery Procedures," 0 (Article Summary in English, article in German), lnformatbnen, pp. 375-396 (Mar. 1991.

Hojjatie et al., "Three-Dimensional Finite Element Analysis of Glass-Ceramic Dental Crowns," J. Biomech., 23(11):1157-1166 (1990.

Huckins, "CAD-CAM Generated Mandibular Model Prototype from MRI Data," AAOMS, p. 96 (1999.

Important Tip About Wearing the Red White & Blue Active Clear Retainer System, Allesee Orthodontic Appliances-Pro Lab, 1 page 1998).

Inside the ADA, JADA, 118:286-294 (Mar. 1989).

JCO Interviews, Craig Andreiko , DDS, MS on the Elan and Orthos Systems, JCO, pp. 459-468 (Aug. 1994.

JCO Interviews, Dr. Homer W. Phillips on Computers in Orthodontic Practice, Part 2, JCO. 1997; 1983:819-831.

Jerrold, "The Problem, Electronic Data Transmission and the Law," AJO-DO, pp. 478-479 (Apr. 1988.

Jones et al., "An Assessment of the Fit of a Parabolic Curve to Pre- and Post-Treatment Dental Arches," Br. J. Orthod., 16:85-93 (1989).

JP Faber et al., "Computerized Interactive Orthodontic Treatment Planning," Am. J. Orthod., 73(1):36-46. Jan. 1978.

Kamada et.al., Construction of Tooth Positioners with LTV Vinyl Silicone Rubber and Some Case KJ Reports, J. Nihon University School of Dentistry (1982) 24(1):1-27.

Kanazawa et al., "Three-Dimensional Measurements of the Occlusal Surfaces of Upper Molars in a Dutch Population," J. Dent Res., 63(11):1298-1301 (Nov. 1984).

Kesling et al., The Philosophy of the Tooth Positioning Appliance, American Journal of Orthodontics and Oral surgery. 1945; 31:297-304.

Kesling, Coordinating the Predetermined Pattern and Tooth Positioner with Conventional Treatment, KN Am. J. Orthod. Oral Surg. (1946) 32:285-293.

Ki Kamada et.al., Case Reports on Tooth Positioners Using LTV Vinyl Silicone Rubber, J. Nihon University School of Dentistry (1984) 26(1): 11-29.

Kleeman et al., The Speed Positioner, J. Clin. Orthod. (1996) 30:673-680.

Kochanek, "Interpolating Splines with Local Tension, Continuity and Bias Control," Computer Graphics, ri 18(3):33-41 (Jul. 1984).

KM Oral Surgery (1945) 31 :297-30.

Kunii et al., "Articulation Simulation for an Intelligent Dental Care System," Displays 15:181-188 (1994).

Kuroda et al., Three-Dimensional Dental Cast Analyzing System Using Laser Scanning, Am. J. Orthod. Dentofac. Orthop. (1996) 110:365-369.

Laurendeau, et al., "A Computer-Vision Technique for the Acquisition and Processing of 3-D Profiles of 7 KR Dental Imprints: An Application in Orthodontics," IEEE Transactions on Medical Imaging, 10(3):453-461 (Sep. 1991.

Leinfelder, et al., "A New Method for Generating Ceramic Restorations: a CAD-CAM System," J. Am. 1-1 Dent. Assoc., 118(6):703-707 (Jun. 1989.

Manetti, et al., "Computer-Aided Cefalometry and New Mechanics in Orthodontics," (Article Summary in English, article in German), Fortschr Kieferorthop. 44, 370-376 (Nr. 5), 1983.

McCann, "Inside the ADA," J. Amer. Dent. Assoc., 118:286-294 (Mar. 1989.

(56) References Cited

OTHER PUBLICATIONS

McNamara et al., "Invisible Retainers," J. Cfin. Orthod., pp. 570-578 (Aug. 1985).
McNamara et al., Orthodontic and Orthopedic Treatment in the Mixed Dentition, Needham Press, pp. 347-353 (Jan. 1993).
Moermann et al., "Computer Machined Adhesive Porcelain Inlays: Margin Adaptation after Fatigue Stress," IADR Abstract 339, J. Dent. Res., 66(a):763 (1987).
Moles, "Correcting Mild Malalignments—As Easy As One, Two, Three," AOA/Pro Corner, vol. 11, No. 1, 2 pages (2002).
Mormann et al., "Marginale Adaptation von adhasuven Porzellaninlays in vitro," Separatdruck aus: Schweiz. Mschr. Zahnmed. 95: 1118-1129, 1985.
Nahoum, "The Vacuum Formed Dental Contour Appliance," N. Y. State Dent. J., 30(9):385-390 (Nov. 1964).
Nash, "CEREC CAD/CAM Inlays: Aesthetics and Durability in a Single Appointment," Dent. Today, 9(8):20, 22-23 (Oct. 1990).
Nishiyama et al., "A New Construction of Tooth Repositioner by LTV Vinyl Silicone Rubber," J. Nihon Univ. Sch. Dent., 19(2):93-102 (1977).
Paul et al., "Digital Documentation of Individual Human Jaw and Tooth Forms for Applications in Orthodontics, Oral Surgery and Forensic Medicine" Proc. of the 24th Annual Conf. of the IEEE Industrial Electronics Society (IECON '98), Sep. 4, 1998, pp. 2415-2418.
Pinkham, "Foolish Concept Propels Technology," Dentist, 3 pages total, Jan./Feb. 1989.
Pinkham, "Inventor's CAD/CAM May Transform Dentistry," Dentist, 3 pages total, Sep. 1990.
Ponitz, "Invisible Retainers," Am. J. Orthod., 59(3):266-272 (Mar. 1971).
Procera Research Projects, "Procera Research Projects 1993 Abstract Collection," pp. 3-7; 28 (1993).
Proffit et al., Contemporary Orthodontics, (Second Ed.), Chapter 15, Mosby Inc., pp. 470-533 (Oct. 1993).
Raintree Essix & ARS Materials, Inc., Raintree Essix, Technical Magazine Table of contents and q Essix Appliances, <httpz;//www.essix.com/magazine/defaulthtml> Aug. 13, 1997.
Redmond et al., "Clinical Implications of Digital Orthodontics," Am. J. Orthod. Dentofacial Orthop., 117(2):240-242 (2000).
Rekow et al., "CAD/CAM for Dental Restorations—Some of the Curious Challenges," IEEE Trans. Biomed. Eng., 38(4):314-318 (Apr. 1991.
Rekow et al., "Comparison of Three Data Acquisition Techniques for 3-D Tooth Surface Mapping," LM Annual International Conference of the IEEE Engineering in Medicine and Biology Society, 13(1):344-345 1991.
Rekow, "A Review of the Developments in Dental CAD/CAM Systems," (contains references to LN Japanese efforts and content of the papers of particular interest to the clinician are indicated with a one line summary of their content in the bibliography), Curr. Opin. Dent., 2:25-33 (Jun. 1992.
Rekow, "CAD/CAM in Dentistry: A Historical Perspective and View of the Future," J. Can. Dent. Assoc., 58(4):283, 287-288 (Apr. 1992.
Rekow, "Computer-Aided Design and Manufacturing in Dentistry: A Review of the State of the Art," J. Prosthet. Dent., 58(4):512-516 (Oct. 1987.
Rekow, "Dental CAD-CAM Systems: What is the State of the Art?", J. Amer. Dent. Assoc., 122:43-48 1991.
Rekow, "Feasibility of an Automated System for Production of Dental Restorations, Ph.D. Thesis," Univ. of Minnesota, 244 pages total, Nov. 1988.
Richmond et al., "The Development of a 3D Cast Analysis System," Br. J. Orthod., 13(1):53-54 (Jan. 1986).
Richmond et al., "The Development of the PAR Index (Peer Assessment Rating): Reliability and Validity," Eur. J. Orthod., 14:125-139 (1992).
Richmond, "Recording the Dental Cast in Three Dimensions," Am. J. Orthod. Dentofacial Orthop., 92(3):199-206 (Sep. 1987).
Rudge, "Dental Arch Analysis: Arch Form, A Review of the Literature," Eur. J. Orthod., 3(4):279-284 1981.
Sakuda et al., "Integrated Information-Processing System in Clinical Orthodontics: An Approach with Use of a Computer Network System," Am. J. Orthod. Dentofacial Orthop., 101(3): 210-220 (Mar. 1992).
Schellhas et al., "Three-Dimensional Computed Tomography in Maxillofacial Surgical Planning," Arch. Otolamp!. Head Neck Sur9., 114:438-442 (Apr. 1988).
Schroeder et al., Eds. The Visual Toolkit, Prentice Hall PTR, New Jersey (1998) Chapters 6, 8 & 9, (pp. 153-210,309-354, and 355-428, respectively.
Shilliday, (1971). Minimizing finishing problems with the minipositioner, Am. J. Orthod. 59:596-599.
Siemens, "CEREC—Computer-Reconstruction," High Tech in der Zahnmedizin, 14 pages total (2004).
Sinclair, "The Readers' Corner," J. Clin. Orthod., 26(6):369-372 (Jun. 1992.
Sirona Dental Systems GmbH, CEREC 3D, Manuel utiiisateur, Version 2.0X (in French), 2003,114 pages total.
Stoll et al., "Computer-aided Technologies in Dentistry," (article summary in English, article in German), Dtsch Zahna'rztl Z 45, pp. 314-322 (1990).
Sturman, "Interactive Keyframe Animation of 3-D Articulated Models," Proceedings Graphics Interface '84, May-Jun. 1984, pp. 35-40.
The Choice Is Clear: Red, White & Blue . . . The Simple, Affordable, No-Braces Treatment, Allesee HI Orthodontic Appliances-Pro Lab product information for doctors. http://ormco.com/aoa/appliancesservices/RWB/doctorhtml>, 5 pages (May 19, 2003).
The Choice is Clear: Red, White & Blue . . . The Simple, Affordable, No-Braces Treatment, Allesee HJ Orthodontic Appliances-Pro Lab product information for patients, <http://ormco.com/aoa/appliancesservices/RWB/patients.html>, 2 pages (May 19, 2003).
The Choice Is Clear: Red, White & Blue . . . The Simple, Affordable, No-Braces Treatment, Allesee Orthodontic Appliances-Pro Lab product information, 6 pages (2003).
The Red, White & Blue Way to Improve Your Smile! Allesee Orthodontic Appliances-Pro Lab product information for patients, 2 pages 1992.
Truax L., "Truax Clasp-Less(TM) Appliance System," Funct. Orthod., 9(5):22-4, 26-8 (Sep.-Oct. 1992).
Tru-Tain Orthodontic & Dental Supplies, Product Brochure, Rochester, Minnesota 55902, 16 pages total (1996).
U.S. Department of Commerce, National Technical Information Service, "Automated Crown Replication Using Solid Photography SM," Solid Photography Inc., Melville NY, Oct. 1977, 20 pages total.
U.S. Department of Commerce, National Technical Information Service, "Holodontography: An Introduction to Dental Laser Holography," School of Aerospace Medicine Brooks AFB Tex, Mar. 1973, 37 pages total.
U.S. Appl. No. 60/050,342, filed Jun. 20, 1997, 41 pages total.
Van Der Linden et al., "Three-Dimensional Analysis of Dental Casts by Means of the Optocom," J. Dent. Res., p. 1100 (Jul.-Aug. 1972).
Van Der Linden, "A New Method to Determine Tooth Positions and Dental Arch Dimensions," J. Dent. Res., 51(4):1104 (Jul.-Aug. 1972).
Van Der Zel, "Ceramic-Fused-to-Metal Restorations with a New CAD/CAM System," Quintessence Int., 24(11):769-778 (1993.
Varady et al., "Reverse Engineering of Geometric Models—An Introduction," Computer-Aided Design, 29(4):255-268,1997.
Verstreken et al., "An Image-Guided Planning System for Endosseous Oral Implants," IEEE Trans. Med. Imaging, 17(5):842-852 (Oct. 1998.
Warunek et al., Physical and Mechanical Properties of Elastomers in Orthodonic Positioners, Am J. Orthod. Dentofac. Orthop, vol. 95, No. 5, (May 1989) pp. 399-400.
Warunek et.al., Clinical Use of Silicone Elastomer Applicances, JCO (1989) XXIII(10):694-700.
Wells, Application of the Positioner Appliance in Orthodontic Treatment, Am. J. Orthodont. (1970) 58:351-366.
Williams, "Dentistry and CAD/CAM: Another French Revolution," J. Dent. Practice Admin., pp. 2-5 (Jan./Mar. 1987.

(56) References Cited

OTHER PUBLICATIONS

Williams, "The Switzerland and Minnesota Developments in CAD/CAM," J. Dent. Practice Admin., pp. 50-55 (Apr./Jun. 1987.

Wishan, "New Advances in Personal Computer Applications for Cephalometric Analysis, Growth Prediction, Surgical Treatment Planning and Imaging Processing," Symposium: Computerized Facial Imaging in Oral and Maxilofacial Surgery Presented on Sep. 13, 1990.

WSCG'98—Conference Program, "The Sixth International Conference in Central Europe on Computer Graphics and Visualization '98," Feb. 9-13, 1998, pp. 1-7, retrieved from the Internet on Nov. 5, 2004, URL<http://wscg.zcu.cz/wscg98/wscg98.h>.

Xia et al., "Three-Dimensional Virtual-Reality Surgical Planning and Soft-Tissue Prediction for Orthognathic Surgery," IEEE Trans. Inf. Technol. Biomed., 5(2):97-107 (Jun. 2001.

Yamamoto et al., "Optical Measurement of Dental Cast Profile and Application to Analysis of Three-Dimensional Tooth Movement in Orthodontics," Front. Med. Biol. Eng., 1(2):119-130 (1988).

Yamamoto et al., "Three-Dimensional Measurement of Dental Cast Profiles and Its Applications to Orthodontics," Conf. Proc. IEEE Eng. Med. Biol. Soc., 12(5):2051-2053 (1990).

Yamany et al., "A System for Human Jaw Modeling Using Intra-Oral Images," Proc. of the 20th Annual Conf. of the IEEE Engineering in Medicine and Biology Society, Nov. 1, 1998, vol. 2, pp. 563-566.

Yoshii, "Research on a New Orthodontic Appliance: The Dynamic Positioner (D.P.); I. The D.P. Concept and Implementation of Transparent Silicone Resin (Orthocon)," Nippon Dental Review, 452:61-74 (Jun. 1980.

Yoshii, "Research on a New Orthodontic Appliance: The Dynamic Positioner (D.P.); II. The D.P. Manufacturing Procedure and Clinical Applications," Nippon Dental Review, 454:107-130 (Aug. 1980).

Yoshii, "Research on a New Orthodontic Appliance: The Dynamic Positioner (D.P.); III.—The General Concept of the D.P. Method and Its Therapeutic Effect, Part 2. Skeletal Reversed Occlusion Case Reports," Nippon Dental Review, 458:112-129 (Dec. 1980.

Yoshii, "Research on a New Orthodontic Appliance: The Dynamic Positioner (D.P.); III. The General Concept of the D.P. Method and Its Therapeutic Effect, Part 1, Dental and Functional Reversed Occlusion Case Reports," Nippon Dental Review, 457:146-164 (Nov. 1980).

You May Be a Candidate for This Invisible No-Braces Treatment, Allesee Orthodontic Appliances-Pro Lab product information for patients, 2 pages (2002).

* cited by examiner

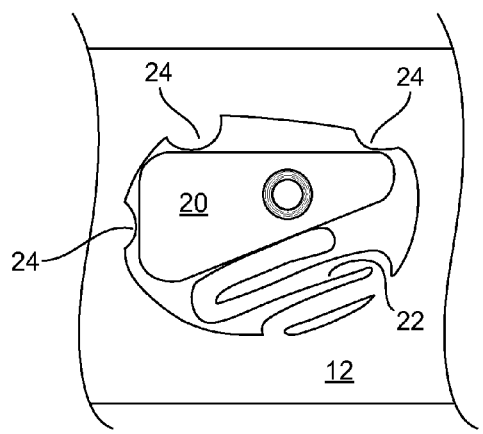
FIG. 3
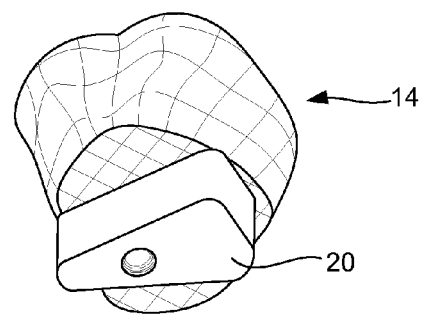
FIG. 4
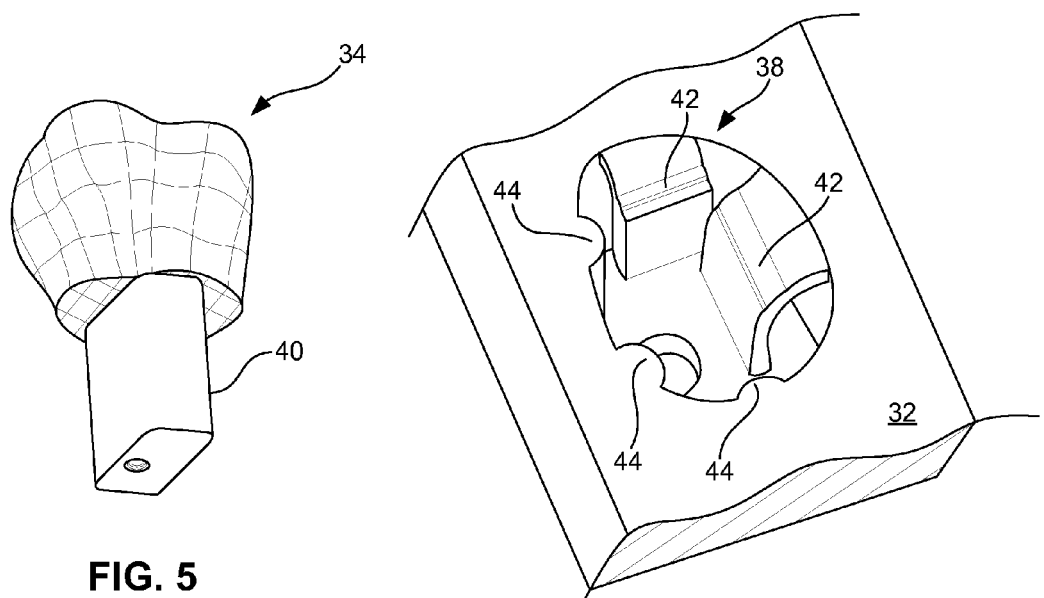
FIG. 5
FIG. 6

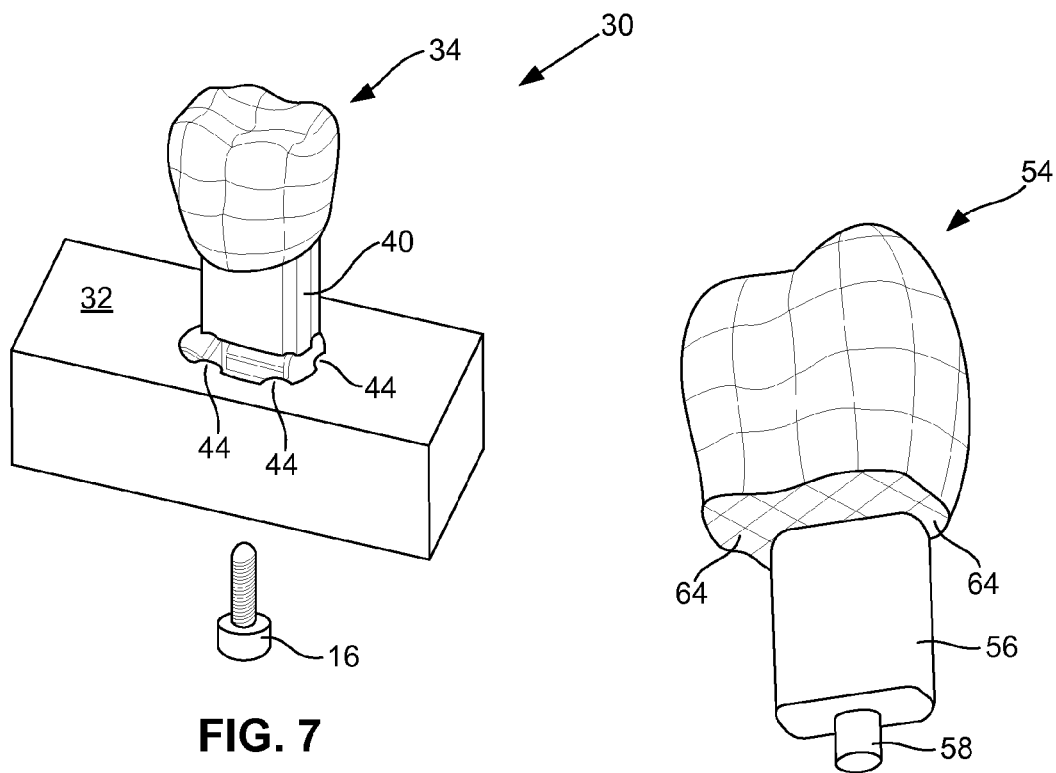
FIG. 7
FIG. 8
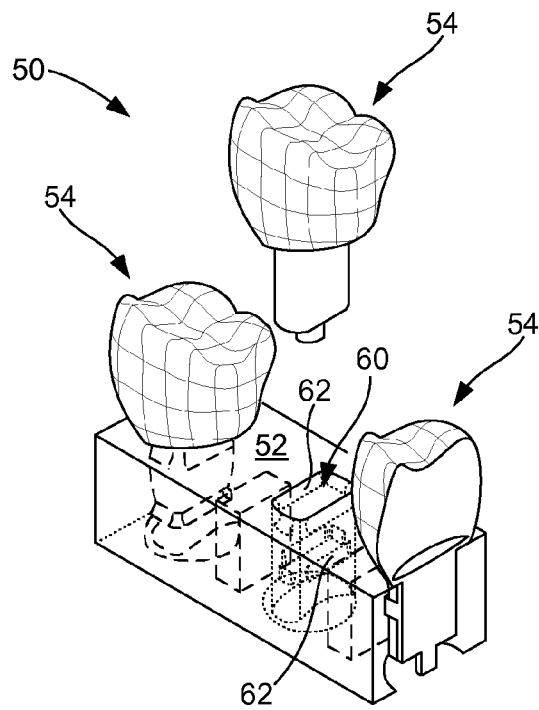
FIG. 9

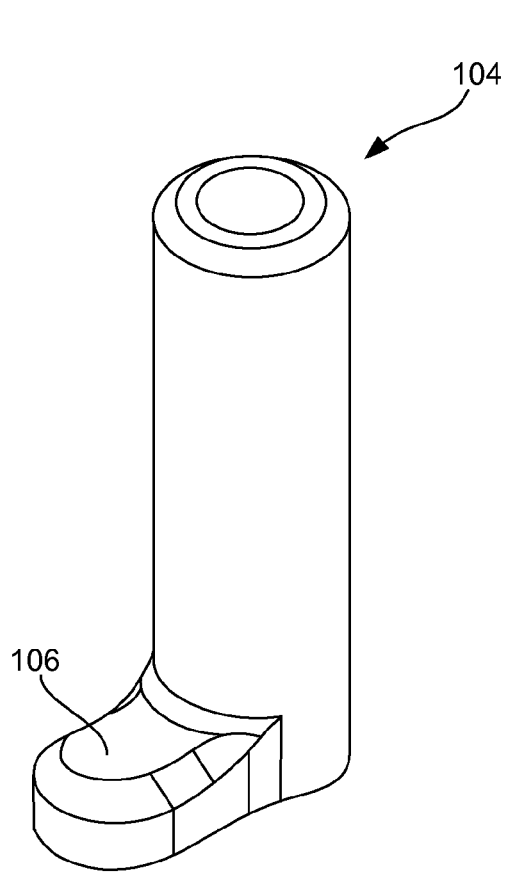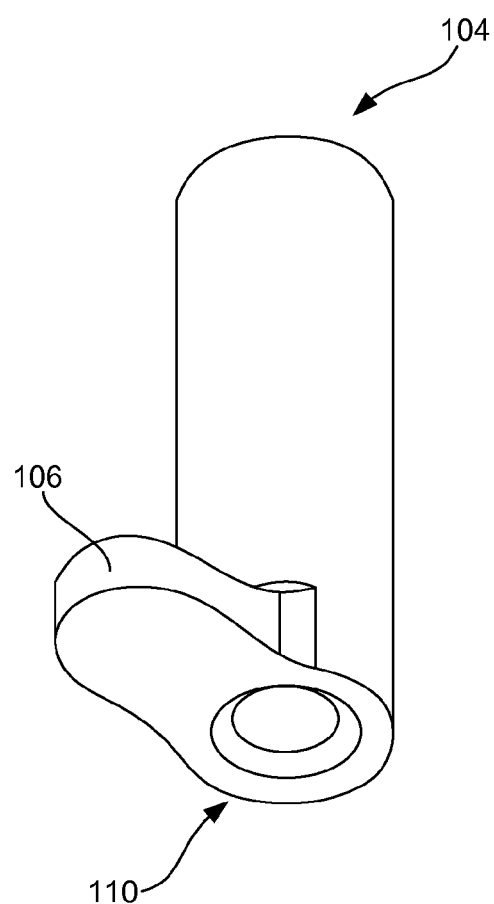
FIG. 25  FIG. 26

DENTAL MODELS AND RELATED METHODS

CROSS-REFERENCE

This application claims the benefit of U.S. Provisional Application No. 61/601,448, filed Feb. 21, 2012, which application is incorporated herein by reference.

BACKGROUND OF THE INVENTION

The present invention relates generally to dental models, and more particularly to dental models having a jaw component and demountable components, such as tooth components and/or implant analogue components, that can be accurately mounted to the jaw component and removed multiple times. In many embodiments, the dental models disclosed herein can be fabricated using additive manufacturing techniques such as stereo-lithography (SLA) and three-dimensional printing.

In the preparation of dental crowns, bridges, and implants, a physical model of the jaw is often used. These jaw models represent the patient's jaw in the vicinity of the crown(s), bridge(s), or implant(s) being prepared. Existing approaches for the preparation of these jaw models have included milling the jaw model from a solid block of material. Such milled jaw models, however, lack desirable features, such as demountable portions that can be accurately positioned when mounted and selectively removed to better facilitate the preparation of the applicable dental crown, bridge, and/or implant.

Thus, improved dental models and related methods are desirable, particularly dental models with demountable portions that can be repeatedly accurately mounted and demounted.

SUMMARY OF THE INVENTION

The following presents a simplified summary of some embodiments of the invention in order to provide a basic understanding of the invention. This summary is not an extensive overview of the invention. It is not intended to identify key/critical elements of the invention or to delineate the scope of the invention. Its sole purpose is to present some embodiments of the invention in a simplified form as a prelude to the more detailed description that is presented later.

The present invention includes dental models, as well as related systems and methods, including methods of use and manufacture or fabrication. In one embodiment, a dental model can include a first component configured to represent a portion of a patient's jaw and a second component that is demountably attachable to the first component. The second component can represent a dental structure of interest, such as the remaining portion of a tooth or a dental implant. The interface between the first and second components includes contact with locally protruding portions on the first component and/or on the second component. In many embodiments, the first component defines a socket and the second component includes a shaft that is received by the socket and interfaces with the socket. The locally protruding portions provide increased compliance that accommodates a design range of interference fit between the first and second components.

For a fuller understanding of the nature and advantages of the present invention, reference should be made to the ensuing detailed description and accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 3 is a cross-sectional view through the socket, the shaft portion of the tooth component, and the folded spring.

FIG. 4 shows the tooth component of the dental model of FIG. 1.

FIG. 5 shows a dental model tooth component, in accordance with many embodiments, that has a rectangular-shaped shaft portion.

FIG. 6 shows a dental model jaw component having a socket configured to receive the tooth component of FIG. 5, in accordance with many embodiments.

FIG. 7 is an exploded view showing a portion of a dental model, in accordance with many embodiments, that includes the tooth component of FIG. 5, the jaw component of FIG. 6, and a screw that mates with the tooth component rectangular-shaped shaft.

FIG. 8 shows a dental model tooth component, in accordance with many embodiments, that has a generally rectangular-shaped shaft portion having a projection portion that may be used to verify insertion depth.

FIG. 9 is a partially exploded view showing a portion of a dental model, in accordance with many embodiments, that includes a jaw component having sockets each with four opposing pairs of compliance features, and tooth components in accordance with the tooth component of FIG. 8.

FIG. 24 through FIG. 26 show dental model implant analog components, in accordance with many embodiments, that have a tab feature that mates with a corresponding slot in jaw component.

DETAILED DESCRIPTION OF THE INVENTION

Figure 1:
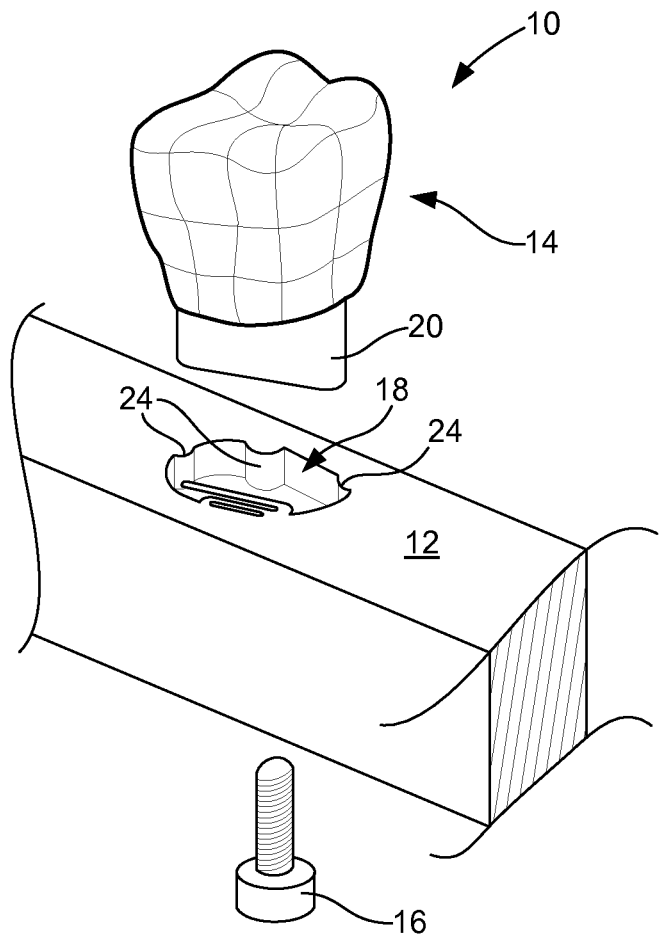
FIG. 1 is an exploded view showing a portion of a dental model, in accordance with many embodiments, that includes a jaw component having a socket with a folded spring, a tooth component having a shaft portion configured for insertion into the socket, and a screw that mates with the shaft.
Figure 2:
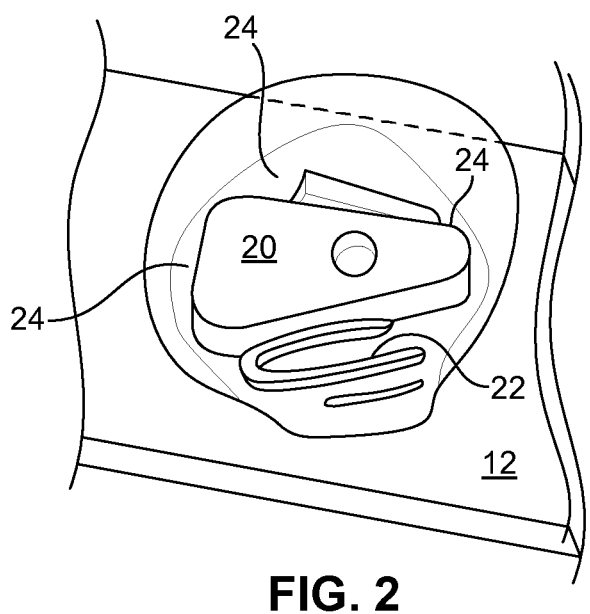
FIG. 2 shows the dental model of FIG. 1 with the tooth portion of the tooth component shown as semi-transparent to show interface details between the shaft and the socket, including contact between the folded spring and the shaft.
Figure 10:
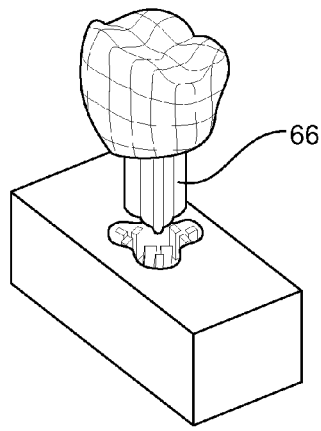
FIG. 10 is an exploded view showing a portion of a dental model, in accordance with many embodiments, that includes a jaw component having a socket with sets of cantilevered springs and a tooth component having a three-lobed "tripod" shaft portion.
Figure 11:
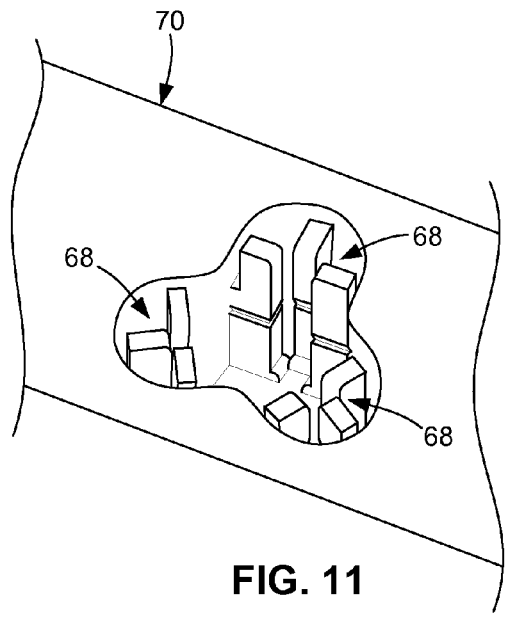
FIG. 11 shows the socket of the jaw component of FIG. 10.
Figure 12:
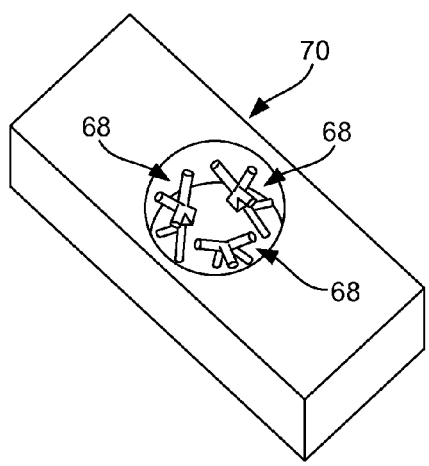
FIG. 12 shows a socket of a jaw component, in accordance with many embodiments, configured to receive a three-lobed "tripod" shaft portion of a tooth component such as the tooth component of FIG. 10.
Figure 13:
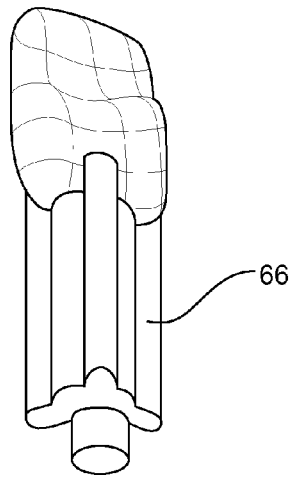
FIG. 13 shows a tooth component, in accordance with many embodiments, having a three-lobed "tripod" shaft portion having a projection portion that may be used to verify insertion depth.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

In the preparation of dental crowns, bridges, and implants, a physical model of the jaw of a patient is often used. The physical model can include one or more preparations and/or one or more input analogs, as appropriate for the application. In the past, these models were generally milled from a solid block of material.

Advantageously, the dental models disclosed herein can be made using additive manufacturing (AM) techniques such as stereolithography (SLA) and 3D printing. The difference in material properties and the manufacturing techniques for dental models that can be made using AM techniques as compared to traditional milled dental models give rise to different requirements and priorities in the design of the models. If, however, a material used to fabricate a dental model as disclosed herein has suitable mechanical properties, the dental model may also be fabricated using existing milling techniques. Constraints on model geometry associated with existing milling techniques, however, may limit the application of existing milling techniques in the fabrication of the dental models disclosed herein.

The models disclosed herein generally include two or more components. One component represents a portion of a patient's jaw in the vicinity of the applicable crown(s), bridge(s), and/or implant(s) to be prepared. This first component is also referred to herein as a jaw component. One or more other components are made that are detachably mountable to the jaw component. These one or more other components represent, for example, each tooth to be crowned and/or each tooth that will support a bridge. These one or more other components can be made to match, typically as closely as possible, the corresponding actual dental geometry of the patient. For example, for the preparation of a crown, a component can represent the geometry of the remaining portion of the tooth to be crowned. Such a component may be referred to herein as a "die" since it can be used as a die to form interfacing portions of the crown that is prepared. Such a component may also be referred to herein as a "tooth component". When dental implants are involved, one or more of these other components can represent the abutment mounting features of the implant(s) as they are located in the patient's jaw. Such components that represent abutment mounting features of an implant(s) may be referred to herein as an "implant analog component." Each of these other components (e.g., die, tooth component, implant analog component) have features configured to interface with corresponding features of the jaw component such that these other components can be repeatedly mounted to the jaw component so as to be accurately located relative to the tooth and gingiva geometry on the jaw component.

In many embodiments, the jaw component includes at least one socket configured to interface with a shaft portion of a die, tooth component, and/or implant analog component. The socket(s) and/or the shaft portion(s) need not be a single continuous shape. For example, the shaft portion can include two separate shaft segments that mate with a socket that includes two corresponding receptacles. And while in the examples and embodiments described herein the socket is generally concave and the shaft is generally convex (as illustrated by the choice of terminology), any other suitable configurations in conformance with the coupling approaches described herein can be used.

To facilitate the fabrication of crowns or bridges, one or more dice and/or one or more tooth analog components may be mounted to and demounted from the jaw component a number of times. One or more implant analog components may also be mounted to and demounted from the jaw component a number of times, though typically only a few times. It is a design goal of the dental models disclosed herein that each time the die, tooth component, and/or implant analog component is inserted that it reach and remain in a position that accurately represents the position of the corresponding preparations and/or implants in the patient's jaw.

Milled dental models are generally made from relatively stiff materials. Properly executed, existing milling techniques can produce a highly accurate finished surface. Existing milling techniques, however, may be limited in their ability to produce small features due to cutter diameter limitations arising from strength, wear, machining time, and cost considerations. In some milled models, the socket and shaft have matching sections taken across insertion direction with the addition of a very small clearance between these two components. Friction between these components is used to keep these components coupled together in a desired relative position. In such a design, a trade-off is made between having a relatively small clearance to keep the position accurate and constant and having a relatively large clearance that may be necessary so that the die, tooth component, and/or analog can be inserted into the socket without friction induced jamming that may arise due to tolerance variations and/or misalignment. Additionally, milled models may also require the use of expensive four- or five-axis milling machines, special cutters (with further diameter limitations), and/or multiple set-ups to create geometry with undercuts as is typical on teeth.

AM materials can have a fairly wide range of mechanical properties. AM materials include suitable polymers. For a dental model geometry that is theoretically machineable, currently available AM machines may not achieve as accurate a surface as is possible by milling. Currently available AM machines are, however, able to produce much smaller concave features than milling and are able to produce undercuts without further special considerations. Although AM machine generated surfaces may have artifacts due to the layering and sometimes lateral resolution, state-of-the-art AM machines can more easily produce small curved details better than existing milling techniques. AM layering effects, however, can cause problems. For example, when two AM fabricated components slide against each other perpendicular to the layering direction, layering effects can create mechanical interlocking that generates high sliding frictional forces.

In the dental models disclosed herein, excessive sliding frictional forces are avoided by including one or more compliant features (or locally protruding portions) as part of the shaft, the socket, or both. The compliant features are configured to accurately locate the shaft in the socket. The compliant features are designed with dimensions and placement to accommodate manufacturing variations in the shaft and socket such that the components can be coupled together in all possible combinations of large and small sockets and shafts without generating too high or too low of the associated interface forces. For example, when a shaft having a minimum dimension is coupled to a socket having a maximum dimension, there is still a suitable level of contact between the compliant portions and their mating features so that the compliant features will have a suitable minimum level of compression, thereby generating a suitable minimum force between the components such that the shaft is not loose in the socket. This minimum force is sufficiently high to generate a friction force sufficient to keep the shaft from moving relative to the socket. In the tightest fit scenario, the compliance features are configured to accommodate the increased level of compression without generating interface forces that are above a suitable level. The compliance features are configured to accommodate the overall range of possible compression levels through a combination of geometry and material properties, examples of which are described herein.

The compliant features (or locally protruding portions) can be configured in a variety of ways, e.g., to include a compliance configured to accommodate an interference fit between the components described herein (e.g., between a jaw component and a tooth component). In some embodiments, the compliant features (or locally protruding portions) can have a compliance (or compression property) that allows for the features to compress when one component (e.g., a jaw component) is engaged with another component (e.g., a tooth component). This compliance (e.g., ability to compress) can be tailored to provide a desired interference fit between the two components.

In certain aspects, the structure and/or position of the compliant features (or locally protruding portions can be configured to achieve a desired interference fit. For example, locally protruding portions can be formed on a shaft portion of a tooth component. The dimensions of the shaft can be configured to fit in a socket of a jaw component. To achieve a desired interference fit between the components, the locally protruding portions can be made to have a structure that expands the local dimensions of the shaft such that there is an overlap between the width of the shaft and the width of the socket. Due at least in part to the configured compliance (or compressive property) of the locally protruding portion, the shaft can be fit securely and accurately in the socket with minimal, if any, movement between the tooth and jaw components. Depending on the properties (e.g., compliance) of a material, the locally protruding portions (or compliant features) can be manufactured to have dimensions that correspond with a given compliance for the material. In an example embodiment, a socket in a jaw component may have a width of about 5 mm. The shaft of the tooth component can similarly have a width of about 5 mm. Owing to, e.g., error in a manufacturing process, the shaft and socket may not fit properly together. Locally protruding portions (or compliant features) can be used to produce a desired interference fit between the two components. For example, a locally protruding portion on the shaft and/or the socket can be made to increase the width of either the shaft and/or socket by a predetermined dimension. In some embodiments, the locally protruding portion (or compliant feature) can be configured to increase the width of the shaft or socket by 50 microns. Due at least in part to the compliance of the locally protruding portion, the locally protruding portion can compress and allow for a desired interference fit between the two components. In some embodiments, the locally protruding portion can be designed to increase dimensions of one component compared to another component over a wide range. For example, a dimension (e.g., width) of one component can be longer than a dimension of a second component over a range, such as between about 10 microns to about 100 microns, between about 20 microns to about 80 microns, or from about 40 microns to about 60 microns. In some embodiments, the dimension of one component (e.g., a shaft of a component) can be different than another component (e.g., a socket) by a predetermined percentage. For example, a width of a shaft at a locally protruding portion can be about 1%, or about 2%, or about 3%, or about 4% or about 5% wider than a socket width. It will be generally recognized by one of ordinary skill in the art that a variety of dimensions can be manufactured and used to tailor both compliance of the protruding portions and/or interference fit between the components. In certain embodiments, the compliance can be tailored according to the material used to make the components and/or by the shape or structure of the compliant feature. For example, folded springs can be used generate compliant features that are more compliant than, e.g., a ridge or ball structure on a component. The spring, e.g., can be structurally designed to compress upon application of force due in-part to the structure of the spring. The ridge or ball structure may have a compliance that is more dependent on the compliance properties of the material used to make the components. The various combinations of compliance for the various compliant features (or locally protruding portions) described herein and tailored interference fit between the various components described herein can be predetermined according to factor such as the properties of the materials, the dimensions of the locally protruding portions, and/or the locations of the locally protruding portions.

Referring now to the drawings, in which like reference numerals represent like parts throughout the several views, FIG. 1 through FIG. 4 illustrate a dental model 10, in accordance with many embodiments, that includes a jaw component 12, a tooth component 14, and a screw 16. The jaw component 12 defines a socket 18. The tooth component 14 has a shaft portion 20 that is received by the socket 18. A serpentine member 22 (folded spring) is formed as an integral part of the jaw component 12 and is disposed within the socket 18. When the shaft portion 20 is mounted in the socket 18, the presence of the shaft portion 20 deflects the serpentine member 22, thereby generating an interface force between the serpentine member 22 and the shaft portion 20. The interface force pushes on a face of the shaft portion 20 that is oriented such that components of the interface force act to register two faces of the shaft portion 20 against three cylindrical portions 24 of the socket 18 to provide repeatable positioning of the shaft portion 20 lateral to the insertion direction of the shaft portion 20. The screw 16 mates with the shaft portion 20 through a hole in the jaw component 12 to anchor the shaft portion 20 securely in the socket 18. The bottom face of the shaft portion 20 is held against the bottom face of the socket 18 (not shown) by the screw 16 to control the position of the shaft portion 20 in the insertion direction relative to the jaw component 12.

FIG. 5 through FIG. 7 illustrate a dental model 30, in accordance with many embodiments. Dental model 30 includes a jaw component 32, a tooth component 34, and a screw 16. The jaw component 32 defines a socket 38. The tooth component 14 has a shaft portion 40 that is received by the socket 38. The dental model 30 is configured similar to the dental model 10, but includes a shaft portion 40 with a generally rectangular shape. Two cantilevered springs 42 are formed as integral parts of the jaw component 32 and are disposed within the socket 38. When the shaft portion 40 is mounted in the socket 38, the presence of the shaft portion 40 deflects each of the cantilevered springs 42, thereby generating an interface force between each of the cantilevered springs 42 and the shaft portion 40. The interface forces push the shaft portion 40 into registration with protruding cylindrical portions 44 of the socket 38 to provide repeatable positioning of the shaft portion 40 lateral to the insertion direction of the shaft portion 40. The screw 16 mates with the shaft portion 40 through a hole in the jaw component 32 to anchor the shaft portion 40 securely in the socket 38. The bottom face of the shaft portion 40 is held against the bottom face of the socket 38 (not shown) by the screw 16 to control the position of the shaft portion 40 in the insertion direction relative to the jaw component 32. Although the screw 16 is used in the dental model 30, any suitable type of fastener can be used.

In the dental models 10, 30, the lateral position accuracy depends on the positional accuracy of the interfacing registration surfaces of the shaft portion and the socket. The lateral position accuracy of existing AM techniques, however, may be insufficient to produce a desired level of positional accuracy. In general, the insertion direction for the shaft portion may not be perpendicular to the AM build layers, so it may not be possible to ensure that side walls of the registration features are exactly aligned with positions that can be built by the AM device (i.e. not between steps of a stepper motor or between counts of an encoder used to position the laser or print head). In this case, better accuracy may be achieved by averaging the errors of opposing faces of the shaft or socket, a concept that can be extended from rectangular through polygons with more sides and also to circular, elliptical, or other shapes.

FIG. 8 and FIG. 9 illustrate a dental model 50, in accordance with many embodiments, that makes use of the opposing compliance concept. Dental model 50 includes a jaw component 52 and multiple tooth components 54. Each tooth component 54 has a generally rectangular-shaped shaft portion 56 having a projection portion 58 that may be used to verify insertion depth. The jaw component 52 defines multiple sockets 60. There are eight compliant features 62 arranged in four opposing pairs in each of the sockets 60 with two pairs near the top of the socket 60 and two near the bottom of the socket 60. In this embodiment, the compliant features 62 are protruding triangular prism portions of the jaw component 52. The triangular prism shape has a non-linear stiffness when compressed towards the side walls of the socket 60 by the shaft portion 56. If opposing compliant features have the same dimensions, the non-linearity strongly favors centering the shaft portion 56 between the opposing compliant features for consistent positioning. In this embodiment, the position in the insertion direction is controlled by pressing a lip 64 at the top of the shaft portion 56 against a flat surface at the top of the socket 60. Friction holds each of the tooth components 54 in place when mounted to the jaw component 52.

FIG. 10 through FIG. 13 illustrate components of dental models that use a three-lobed "tripod" shaft 66. Each lobe interacts with a set of cantilever springs 68 built into a socket 70. The cantilever springs can be easily reconfigured to tune their compliance behavior, but their relatively small dimensions place higher requirements on the material properties to maintain integrity.

Figure 14:
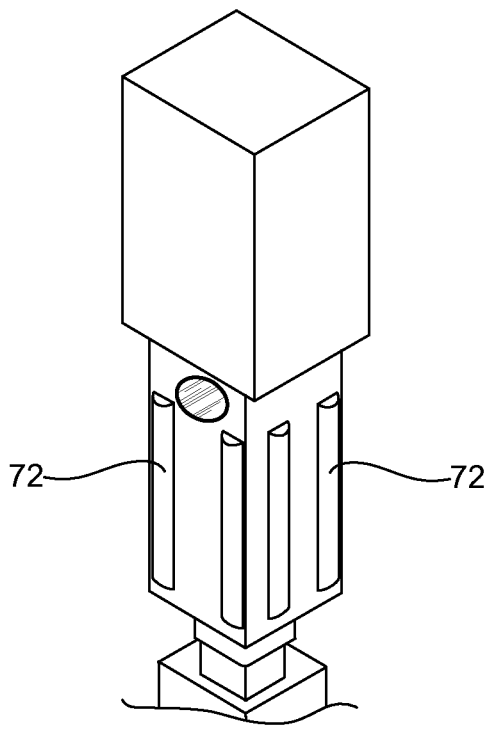
FIG. 14 shows a dental model component, in accordance with many embodiments, having a rectangular-shaped shaft having longitudinal compliance features and with a projection portion that may be used to verify insertion depth.
Figure 15:
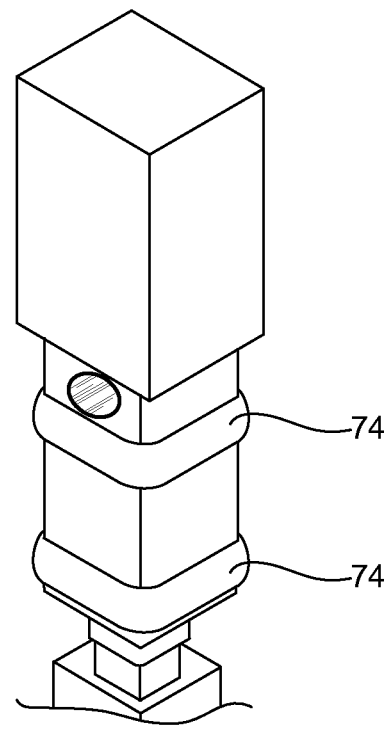
FIG. 15 shows a dental model component, in accordance with many embodiments, having a rectangular-shaped shaft having upper and lower transversely-oriented compliance features and with a projection portion that may be used to verify insertion depth.

FIG. 14 and FIG. 15 show variations on the rectangular shaft. In these embodiments, the compliant features are part of the shaft instead of the socket. In FIG. 14, the compliant features are eight ribs 72 extending longitudinally, two on each face of the shaft. The ribs 72 have a generally triangular cross section except that the tip is rounded. A sharp tip may be prone to breakage. In FIG. 15, the compliant features are two ribs 74 extending transversely around the shaft. For longitudinal ribs, the shaft is guided all the way in, but the friction builds as the shaft is inserted and a larger area of the ribs is compressed. If not sized correctly, or if manufacturing tolerances are too loose such that it cannot be sized correctly, the shaft will either be loose in the socket or the friction forces will be high, making insertion and removal difficult. As will be discussed in regards to FIG. 22, the interfacing regions of the shaft and the socket can be "stepped" to avoid overly large contact areas. The use of "stepped" interface regions can be applied in any suitable fashion to any suitable dental model design that includes compliant features.

Figure 16:
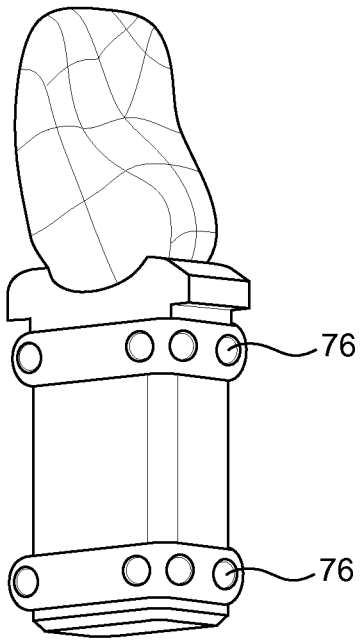
FIG. 16 and FIG. 17 show dental model tooth components, in accordance with many embodiments, having a rectangular-shaped shaft with hollow upper and lower transversely-oriented compliance features and top stop detent features.
Figure 17:
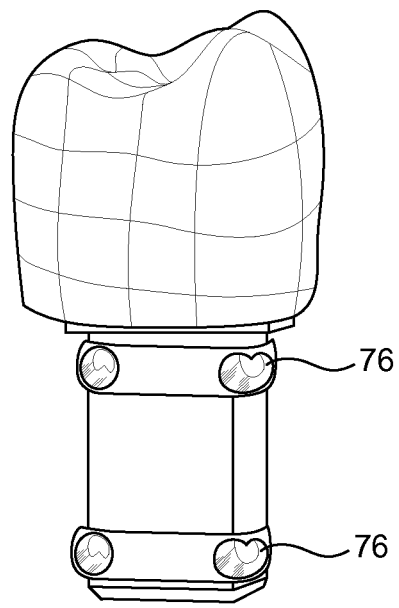
Figure 18:
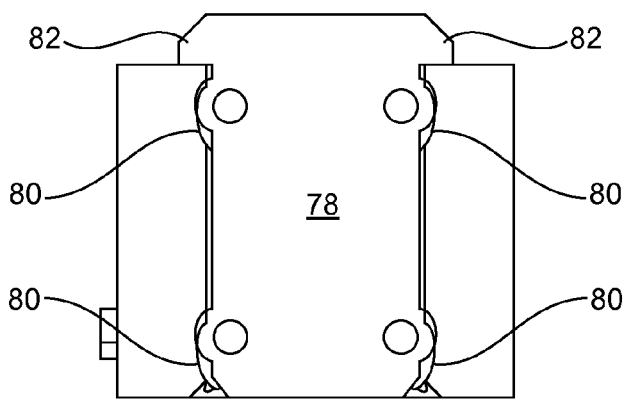
FIG. 18 is a cross-sectional view through a portion of a dental model, in accordance with many embodiments, that includes a dental model component and a jaw component, the dental model component having upper and lower transversely-oriented compliance features and a top stop detent feature, and the jaw component having transversely-oriented sidewall recesses.

FIG. 16 through FIG. 18 show more embodiments that utilize rectangular-shaped shafts. In these embodiments, ribs 76 are hollowed to provide increased compliance relative to solid ribs. In FIG. 18, a shaft portion 78 is shown seated in a socket. The socket has depressions 80 in its surface designed to mate with the ribs 76 to form a snap fit that tends to pull the shaft 78 into a detent position. In this embodiment, a lip 82 at the top of the shaft portion 78 is stopped by the top of the socket before the ribs 76 are fully engaged into the detent position so that the lip 82 determines the final position. The lip 82 can be omitted, in which case, the position in the insertion direction would be determined by the balance of forces between the ribs 76 and the depressions 80 in the socket.

Figure 20:
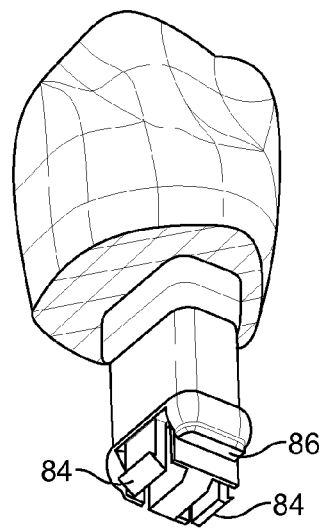
FIG. 20 shows a dental model tooth component, in accordance with many embodiments, that has upper and lower transversely-oriented compliance features, snap-hooks, and bottom stop surfaces.
Figure 19:
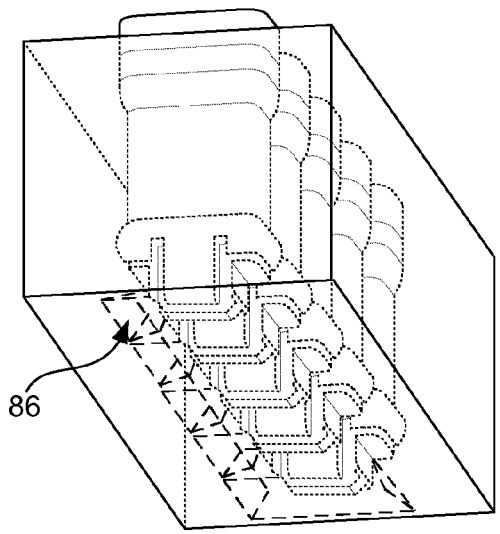
FIG. 19 shows a dental model, in accordance with many embodiments, in which dental model components having upper and lower transversely-oriented compliance features, snap-hooks, and bottom stop surfaces are shown disposed within sockets of a jaw component of the dental model.

FIG. 19 and FIG. 20 show another embodiment similar to those in FIG. 16 through FIG. 18 except that the ribs are not hollowed and a snap fit is generated by separate hooks 84 near the bottom of the shaft that engage with a sloped opening 86 at the bottom of the socket. In many embodiments, the slope of the hook surface and of the mating surface on the socket is configured so that the snap fit is not permanent and the die can be removed easily. It is also possible to configure the slope of the hook surface and of the mating surface on the socket so that the die can only be removed by manipulating a feature on the hook 84 to disengage the hook 84 from the socket. In this embodiment, the position in the insertion direction is determined by the interaction of shoulder surfaces 86 near the bottom of the shaft and mating socket surfaces near the bottom of the socket.

Figure 21:
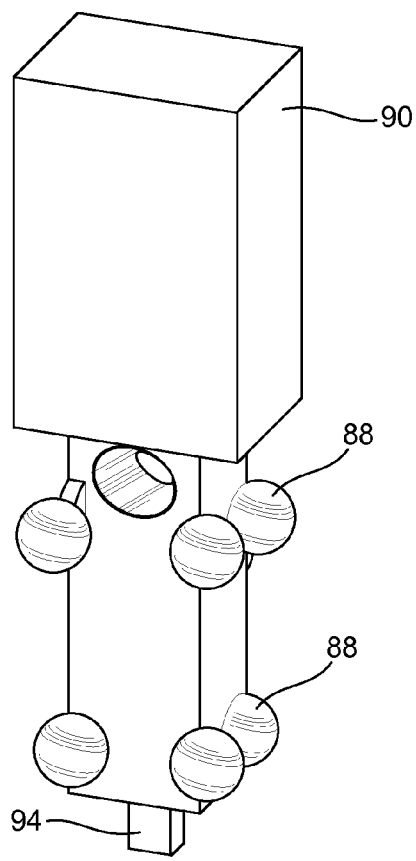
FIG. 21 shows a dental model component, in accordance with many embodiments, that has spherical compliance features and is configured to be received within a socket of a jaw component having stepped sidewalls.
Figure 22:
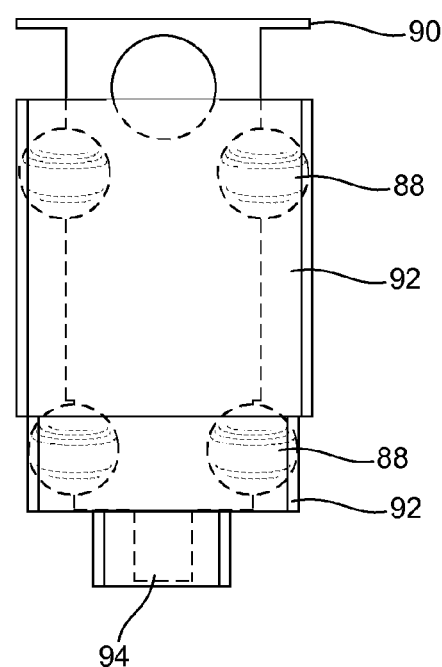
FIG. 22 shows the dental model component of FIG. 21 disposed within a socket of a jaw component having stepped sidewalls, in accordance with many embodiments.

FIG. 21 and FIG. 22 show another embodiment that can be used, for example, for crowns and bridges. In this embodiment, the compliance portion is a set of spherical features 88 on the shaft. The spherical shape has a non-linear stiffness with the advantages discussed above for FIG. 8 and FIG. 9. The compliance is easily manipulated by choosing the radius and amount of overlap of the spherical feature 88 with the body of the shaft. Other suitable shapes can also be used. For example, an ellipsoid can be used with the narrow equators against the socket walls to increase the compliance for a given overall size. As shown, each sphere 88 contacts the socket at two points on adjacent faces of the socket. Alternate embodiments can be configured such that only one point on each sphere 88 makes contact with an adjacent face of the socket. For example, each of the longitudinal ribs in FIG. 14 can be replaced by two spheres, one near the top of the shaft and one near the bottom.

The number of contacts can be reduced, for example, until there are only six contact points, which define a kinematic mount. The addition of a suitably placed seventh contact can create an opposing force on the other contact points, so that the shaft is firmly positioned in the socket, rather than being dependent on an outside force, typically gravity, to ensure that all the contacts remain touching. In practice, because of resolution limitations associated with AM fabrication of a single surface, it may be preferable to use a greater number of opposed contacts to average out the position error of the surfaces.

While most of the embodiments described herein use a rectangular shaft, any other suitable shape, for example a triangular shaft, can also be used. The shaft shape employed can be somewhat independent of the number of contacts. For example, instead of using four contact spheres near the bottom of the shaft and four near the top, three near the bottom and three near the top can be used with each sphere having two points of contact with adjacent faces of the socket. A shaft of any suitable shape (e.g., triangular, rectangular, pentagon, etc.) can be used to connect the spheres.

Note that the hole through the shaft shown in FIG. 21 and FIG. 22 is for prototyping purposes and can be omitted. In these figures, a rectangular prism 90 represents the portion that would have the shape of the preparation. As shown in FIG. 22, the socket has walls 92 parallel to the insertion direction, but the walls 92 are stepped so that the lower set of compliance portions are loose in the socket until they reach the step near the bottom of the socket. This keeps the insertion force near zero until the shaft is almost fully inserted into the socket. A projection 94 at the bottom of the shaft extends through a hole in the jaw component and is positioned and shaped such that its end surface is flush with the bottom of the jaw component. This enables easy checking that the shaft is fully inserted into the socket as any error would be apparent by the unevenness of the projection 94 relative to the bottom of the jaw component. Note that for the contact that sets the position in the insertion direction, high compliance is undesirable unless there are two opposing compliant contacts, as can be provided in an embodiment similar to the embodiment of FIG. 18 but without the lip. For a single contact, a hard stop in the insertion direction provides for well-defined and repeatable positioning.

Most of the embodiments described herein have the compliant features on the shaft. Nearly all of the described embodiments, however, can be reconfigured to place the compliant features on the socket instead. Additional embodiments can use a mixture of locations for the compliant features with some on the shaft and some on the socket. For AM techniques using a solid support material, such as Objet, it may be preferable to put the compliant features on the shaft in order to avoid small concave features from which the support material is difficult to remove, assuming that the shaft is the generally convex and the socket concave as in many embodiments. For other AM techniques, other considerations may guide the choice of where to locate the compliant features.

Figure 23:
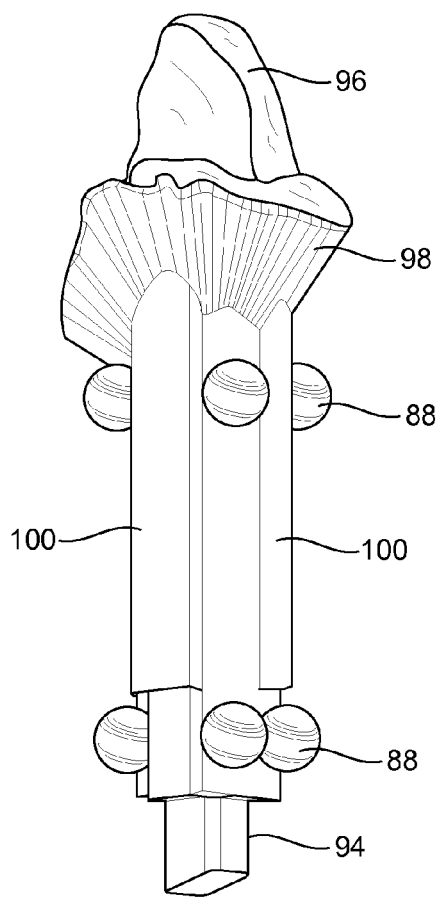
FIG. 23 shows a dental model component, in accordance with many embodiments, has spherical compliance features and longitudinal stiffening ribs disposed between the spherical compliance features.

FIG. 23 shows an improved embodiment of the embodiment of FIG. 21 and FIG. 22 and also illustrates a realistic preparation shape 96 and a generally conical transition 98 from the visible surface to the shaft. In this improved embodiment, ribs 100 have been added between the spherical compliance features to stiffen and strengthen the shaft. Additional material can also be added to any other suitable location of the shaft, for example, all locations of the shaft except immediately adjacent to the upper and lower spheres 88. The ribs 100 are configured to not contact the socket.

Although not shown in many of the embodiments illustrated herein, it may be preferable to configure the contact points such that the die can only be inserted in one orientation. A keying feature can also be used to prevent incorrect orientations.

Implant analog components typically provide mounting features for an abutment that is used to create a crown. The loads on such mounting features can be relatively high making it preferable that the analog be metal. When the analog is metal, cost considerations and material properties may make it preferable to put compliance features in the socket instead of on the analog.

Figure 24:
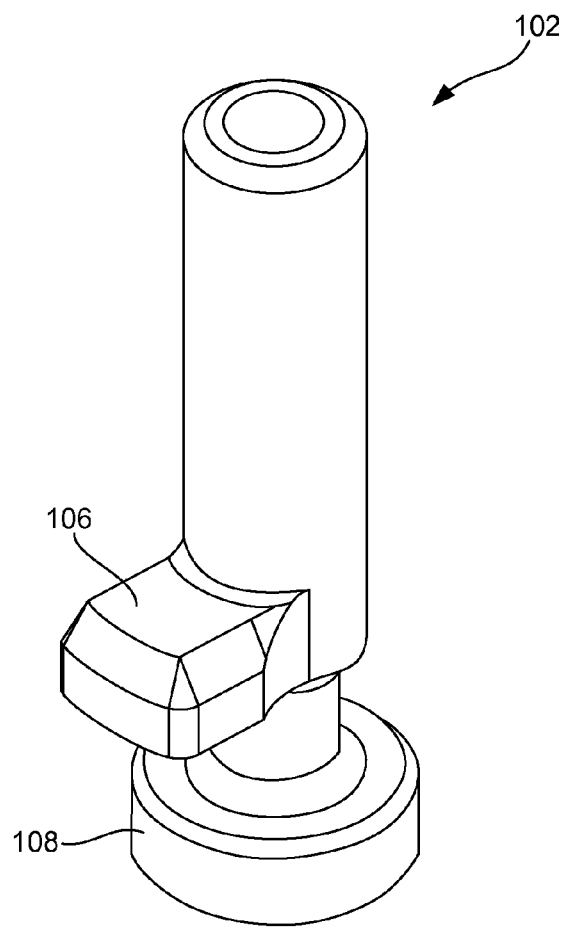

FIG. 24 through FIG. 26 illustrate two implant analog embodiments 102, 104. Each has a single tab feature 106 configured to mate with a corresponding slot in the socket providing a hard stop in the insertion direction and defining the angular position of the analog around the insertion direction. In FIG. 24, a handle 108 is provided for easy removal of the analog 102. In FIG. 26, a tapped hole 110 allows a screw to be used as a temporary handle to remove the analog 104.

Figure 27:
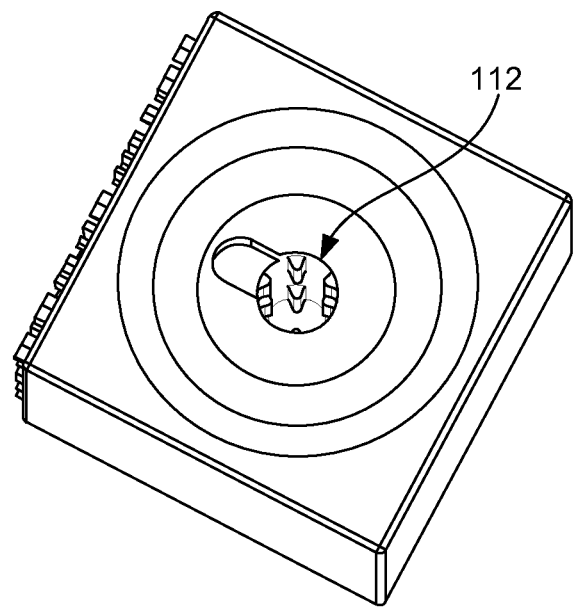
FIG. 27 and FIG. 28 show a dental model jaw component, in accordance with many embodiments, that has a socket with multiple compliance features and an orientation recess.
Figure 28:
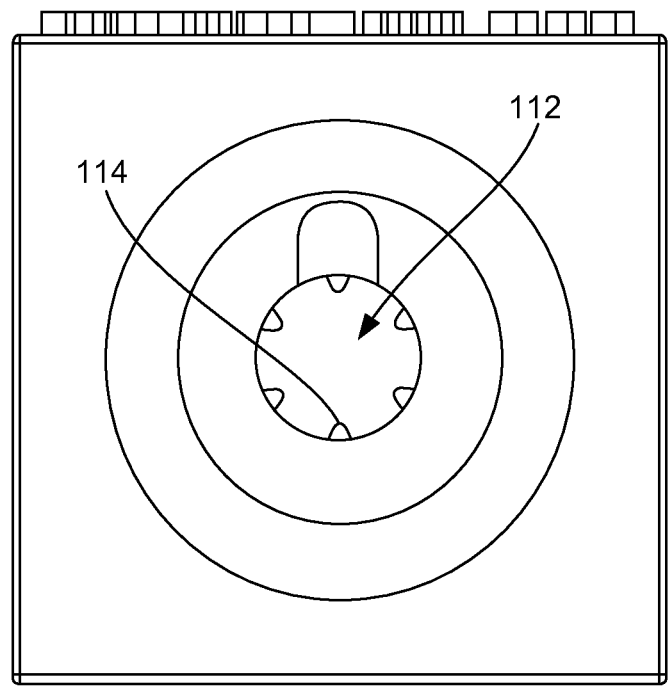
Figure 29:
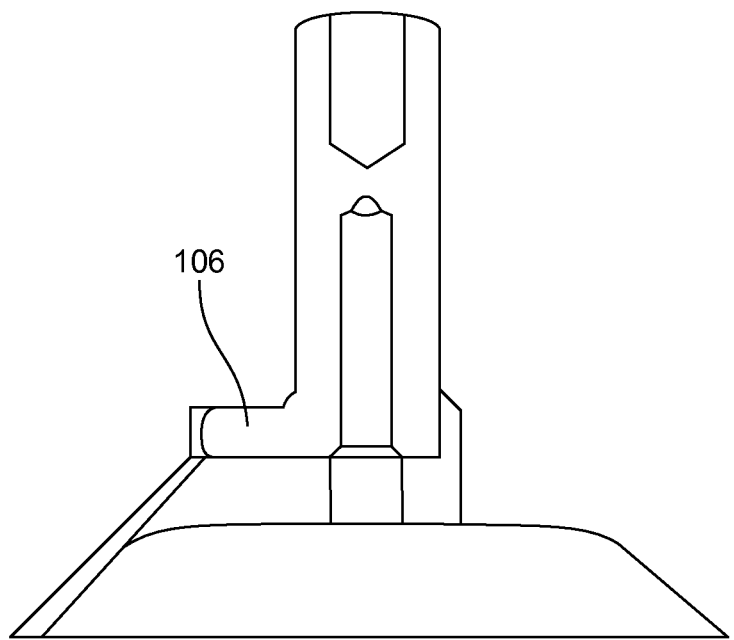
FIG. 29, FIG. 30, and FIG. 32 are cross-sectional views showing a dental model implant analog component mounted in a jaw component, in accordance with many embodiments.
Figure 30:
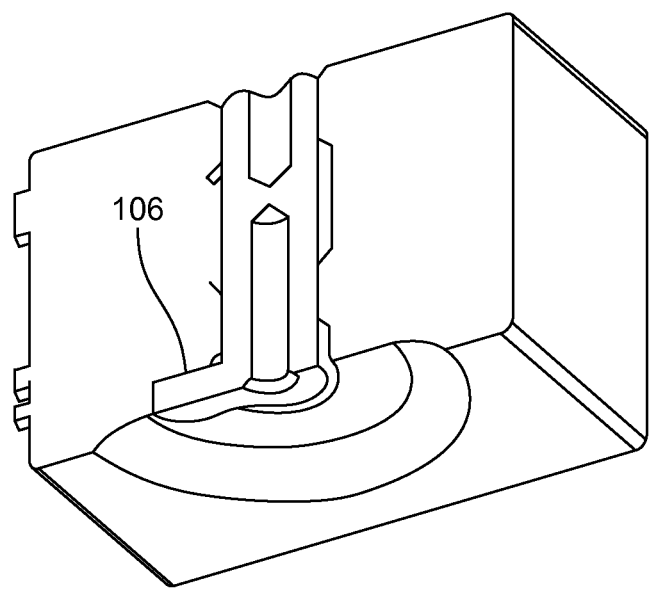
Figure 31:
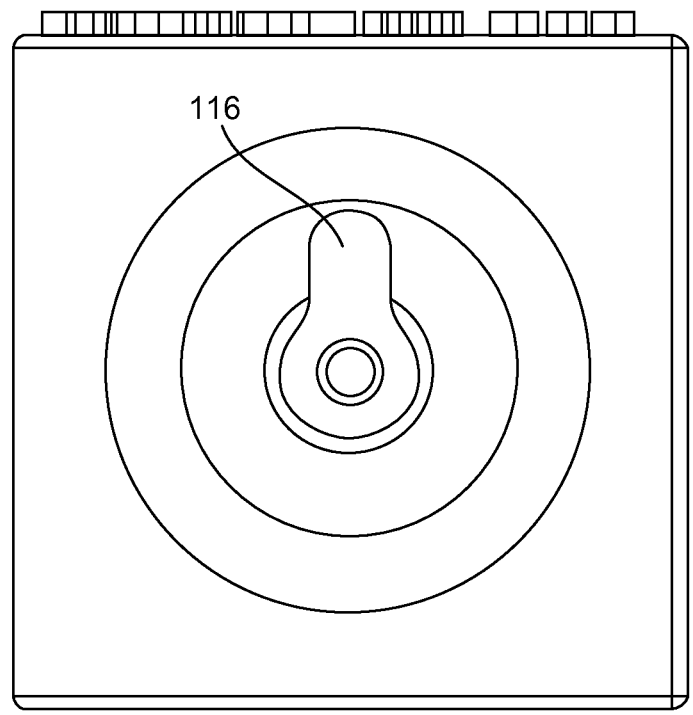
FIG. 31 is a plan view showing a dental model implant analog component mounted in a jaw component, in accordance with many embodiments.
Figure 32:
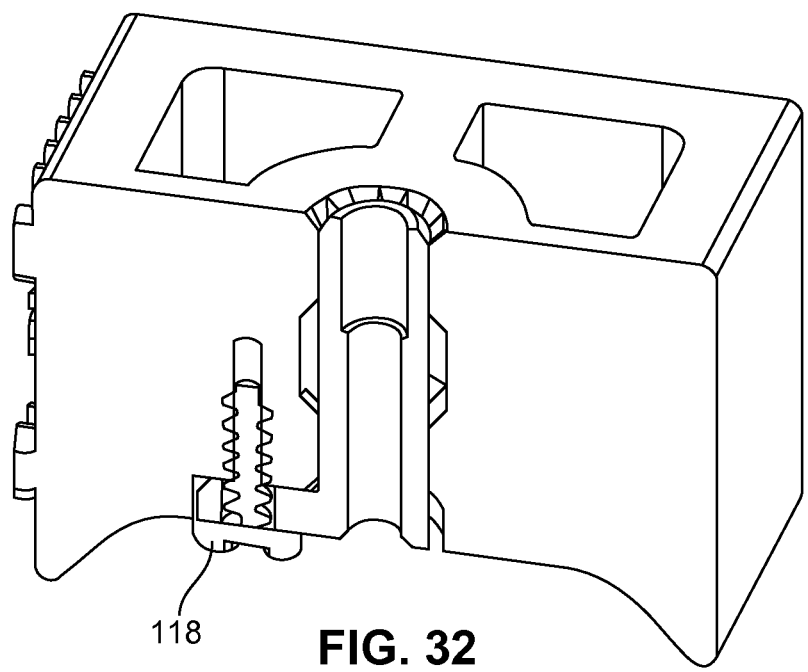

FIG. 27 and FIG. 28 show a socket 112 with multiple compliance portions 114. FIG. 31 shows an implant analog 116 mounted in the socket. FIG. 29 and FIG. 30 show similar embodiments, but without the socket compliance features, and show the top surface of the tab 106 on the analog in contact with the socket to limit the insertion depth. FIG. 32 shows a similar analog mounted in a socket with compliance features. This version adds a screw 118 passing through the analog's tab to provide a firm mounting. The screw 118 prevents inadvertent movement of the analog when an abutment is being mounted on the analog or when a crown is being mounted on the abutment.

Figure 33:
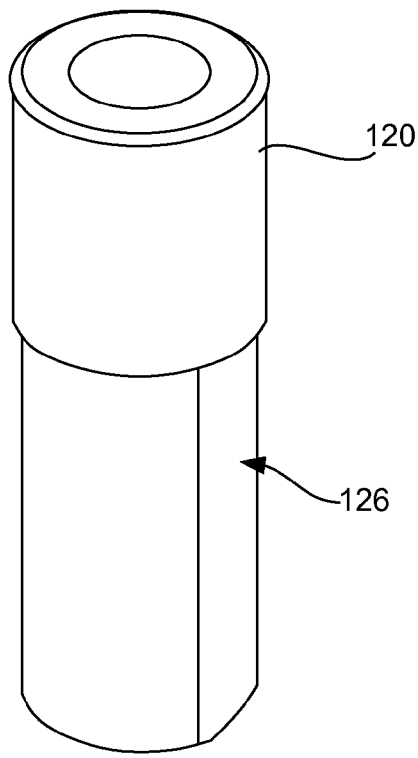
FIG. 33 shows a dental model implant analog component, in accordance with many embodiments, that has a flat side surface for use in orienting the implant analog component relative to a receiving jaw component.
Figure 34:
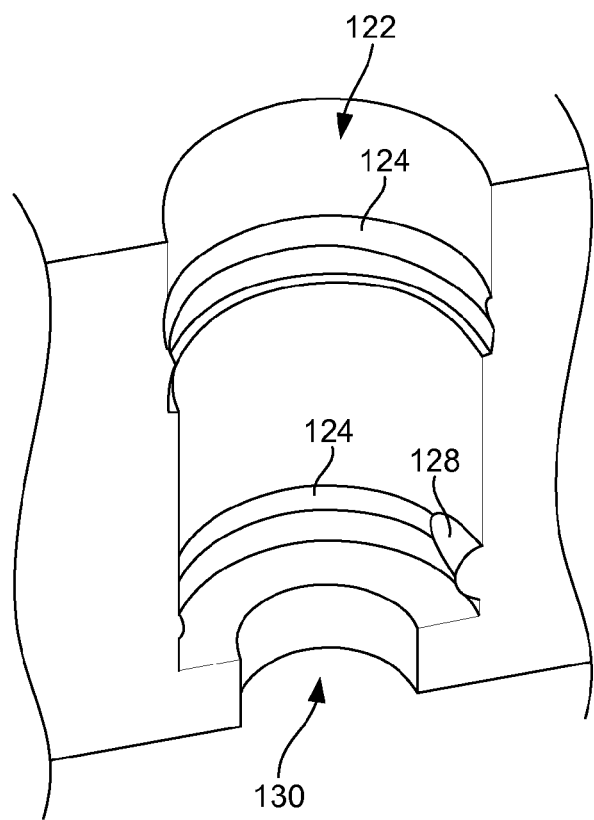
FIG. 34 shows a dental model jaw component, in accordance with many embodiments, that has a socket with an orientation feature, the socket being configured to receive and orient the implant analog component of FIG. 33.

FIG. 33 and FIG. 34 illustrate an embodiment that includes an implant analog 120 and a socket 122 and uses transverse ribs 124 in the socket as the compliant portions. Similar to the embodiment illustrated in FIG. 22, the compliant portions are "stepped" so that the analog 120 can be inserted with almost no force until it is almost seated. The analog 120 has a flat surface 126 that interfaces with a protruding portion 128 of the socket 122 to prevent rotation about the insertion direction. A hole 130 in the bottom of the socket allows a screw to be used to firmly mount the analog 120 in the socket 122. Alternatively, the analog can include a projection, similar to the projection of the embodiment of FIG. 22, that is used to verify the correct insertion depth. When a projection is used, it may be easier and less expensive for the projection's end surface to be perpendicular to the insertion direction and modify the bottom of the jaw model to have a face parallel and flush with that end surface for comparison, rather than having the jaw model bottom be flat and having to cut a custom angle on the analog appropriate for the angle at which the socket is oriented in the jaw model.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A dental model comprising:
   a first component configured to represent a portion of a patient's jaw and defining a socket;
   at least one second component that is demountably attachable to the first component and configured to represent at least one dental structure in the portion of the patient's jaw, the at least one second component including a shaft shaped to be inserted into the socket of the first component along an insertion direction;
   a plurality of locally protruding portions located in the socket and extending laterally to the insertion direction of the shaft so as to form an interface between the first and second components; and
   a spring feature positioned in the socket so as to push the shaft against the plurality of locally protruding portions.

2. The dental model of claim 1, comprising a plurality of the second components.

3. The dental model of claim 1, wherein the plurality of locally protruding portions comprises at least one convex protruding portion.

4. The dental model of claim 1, wherein the spring feature is integrally formed with the first component.

5. The dental model of claim 1, wherein the spring feature comprises a folded spring or a cantilever spring.

6. The dental model of claim 1, further comprising a fastener that engages the shaft to secure the shaft to the socket along the insertion direction for the at least one second component.

7. The dental model of claim 6, wherein the first component comprises a hole shaped to receive the fastener.

8. The dental model of claim 1, wherein the shaft has a substantially rectangular cross-sectional shape perpendicular to the insertion direction of the at least one second component and the socket includes a plurality of integral spring features that push the shaft into contact with the socket.

9. The dental model of claim 1, wherein the shaft has a distal protrusion that is disposed within an aperture in the first component, the distal protrusion having a distal surface that aligns with an external surface of the first component to enable observation that the at least one second component is properly positioned along the insertion direction for the at least one second component.

10. The dental model of claim 1, wherein the shaft has a bottom surface that interfaces with a surface of the socket to position the at least one second component relative to the first component along the insertion direction for the at least one second component.

11. The dental model of claim 1, wherein the shaft and the socket are configured to control orientation of the shaft around an axis of insertion of the at least one second component.

12. The dental model of claim 1, wherein the socket comprises three locally protruding portions and the spring feature pushes the shaft into contact with the three locally protruding portions.

13. The dental model of claim 1, wherein the plurality of locally protruding portions of the socket register the shaft relative to the socket laterally to the insertion direction for the at least one second component.

14. The dental model of claim 1, wherein the spring feature comprises a compliance configured to accommodate an interference fit between the first and second components.

15. The dental model of claim 1, wherein the shaft compresses the spring feature when the shaft is inserted into the socket so as to generate an interface force between the shaft and the spring feature.

16. The dental model of claim 1, wherein the plurality of locally protruding portions are positioned to contact two different faces of the shaft.

17. The dental model of claim 1, further comprising a second spring feature positioned in the socket so as to push the shaft against the plurality of locally protruding portions.

18. The dental model of claim 1, wherein the at least one second component represents a portion of a tooth or a dental implant.

19. The dental model of claim 1, wherein the first component represents a portion of the patient's jaw near a crown, bridge, or implant to be prepared.

20. The dental model of claim 1, wherein the first component comprises a plurality of layers.

* * * * *